(12) United States Patent
Slayton et al.

(10) Patent No.: US 6,623,430 B1
(45) Date of Patent: *Sep. 23, 2003

(54) METHOD AND APPARATUS FOR SAFETY DELIVERING MEDICANTS TO A REGION OF TISSUE USING IMAGING, THERAPY AND TEMPERATURE MONITORING ULTRASONIC SYSTEM

(75) Inventors: Michael H. Slayton, Tempe, AZ (US); Peter G. Barthe, Phoenix, AZ (US); Valeryi Lishko, Mayfield Heights, OH (US)

(73) Assignee: Guided Therapy Systems, Inc., Mesa, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,175

(22) Filed: Feb. 10, 2000

Related U.S. Application Data

(63) Continuation-in-part of application No. 08/950,353, filed on Oct. 14, 1997, now Pat. No. 6,050,943.

(51) Int. Cl.[7] ............................................. A61B 8/00
(52) U.S. Cl. ........................................... 600/439; 601/2
(58) Field of Search ................................. 600/407, 439; 601/2, 3; 607/154, 96; 424/489, 423

(56) References Cited

U.S. PATENT DOCUMENTS

| | | |
|---|---|---|
| 4,101,795 A | 7/1978 | Fukumoto et al. |
| 4,431,008 A | 2/1984 | Wanner et al. |
| 4,513,749 A | 4/1985 | Kino et al. |
| 4,513,750 A | 4/1985 | Heyman et al. |
| 4,566,459 A | 1/1986 | Umemura et al. |
| 4,620,546 A | 11/1986 | Aida et al. |
| 4,754,760 A | 7/1988 | Fukukita et al. |
| 4,757,820 A | 7/1988 | Itoh |

(List continued on next page.)

OTHER PUBLICATIONS

"Applications of Lipid–Coated Microbubble Ultrasonic Contrast to Tumor Therapy"—Simon et al —Ultrasound in Med. & Biol. vol. 19, No. 2, pp. 123–125 (1993).

"Ultrasound–Enhanced Effects of Adriamycin Against Murine Tumors"—Saad et al—Ultrasound in Med. & Biol. vol. 18, No. 8, pp. 715–723 (1992).

"Interaction of Ultrasound and Model Membrane Systems: Analyses and Predictions"—Tata et al—American Chemical Society, Phys. Chem. 1992, 96, pp. 3548–3555.

"Evaluation of the Effect of Cavitation Activity on Drug–Ultrasound Synergisms"—Jeffers et al—1993 IEEE Ultrasonics Symposium, pp. 925–928.

"Application of the Thermal Dose Concept for Predicting the Necrosed Tissue Volume During Ultrasound Surgery"—Damianou et al—1993 IEEE Ultrasound Symposium, pp. 1199–1202.

*Primary Examiner*—Marvin M. Lateef
*Assistant Examiner*—Runa Shah Qaderi
(74) *Attorney, Agent, or Firm*—Snell & Wilmer

(57) ABSTRACT

A method and apparatus for controlling the safe delivery of thermosensitive liposomes containing medicant to a targeted tissue region using ultrasound. Thermosensitive liposomes containing medicants are delivered to a region of interest, the region of interest is located using ultrasound imaging, ultrasound therapy is applied to heat the region of interest, and the temperature of the region is monitored to determine whether a designated threshold temperature has been reached which allows for the release of medicants from the liposomes. If the threshold temperature is reached, and the liposomes are melted, the treatment stops. If the threshold temperature has not been reached, the application of ultrasound therapy and ultrasound imaging are alternated until the threshold temperature is reached. The ultrasound imaging, temperature monitoring and ultrasound therapy are preferably performed with a single transducer.

8 Claims, 13 Drawing Sheets

U.S. PATENT DOCUMENTS

| | | |
|---|---|---|
| 4,801,459 A | 1/1989 | Liburdy |
| 4,807,633 A | 2/1989 | Fry |
| 4,817,615 A | 4/1989 | Fukukita et al. |
| 4,865,042 A | 9/1989 | Umemura et al. |
| 4,891,043 A | 1/1990 | Zeimer et al. |
| 4,900,540 A | 2/1990 | Ryan et al. |
| 4,901,729 A | 2/1990 | Saitoh |
| 4,992,989 A | 2/1991 | Watanabe et al. |
| 5,040,537 A | 8/1991 | Katakura |
| 5,117,832 A * | 6/1992 | Sanghvi et al. ............. 600/459 |
| 5,149,319 A | 9/1992 | Unger |
| 5,190,766 A | 3/1993 | Ishihara |
| 5,205,287 A | 4/1993 | Erbel et al. |
| 5,209,720 A | 5/1993 | Unger |
| 5,215,680 A | 6/1993 | D'Arrigo |
| 5,247,924 A | 9/1993 | Suzuki et al. |
| 5,257,970 A | 11/1993 | Dougherty |
| 5,323,779 A | 6/1994 | Hardy et al. |
| 5,348,016 A | 9/1994 | Unger et al. |
| 5,360,268 A | 11/1994 | Hayashi et al. |
| 5,370,121 A | 12/1994 | Reichenberger et al. |
| 5,380,519 A | 1/1995 | Schneider et al. |
| 5,391,140 A | 2/1995 | Schaetzle et al. |
| 5,391,197 A * | 2/1995 | Burdette et al. ................ 601/3 |
| 5,469,854 A | 11/1995 | Unger et al. |
| 5,526,815 A | 6/1996 | Granz et al. ................ 600/439 |
| 5,558,092 A | 9/1996 | Unger et al. ................ 600/439 |
| 5,580,575 A | 12/1996 | Unger et al. |
| 5,720,287 A * | 2/1998 | Chapelon et al. ........... 600/439 |
| 5,762,066 A * | 6/1998 | Law et al. .................. 600/439 |
| 5,810,888 A * | 9/1998 | Fenn .......................... 600/407 |

\* cited by examiner

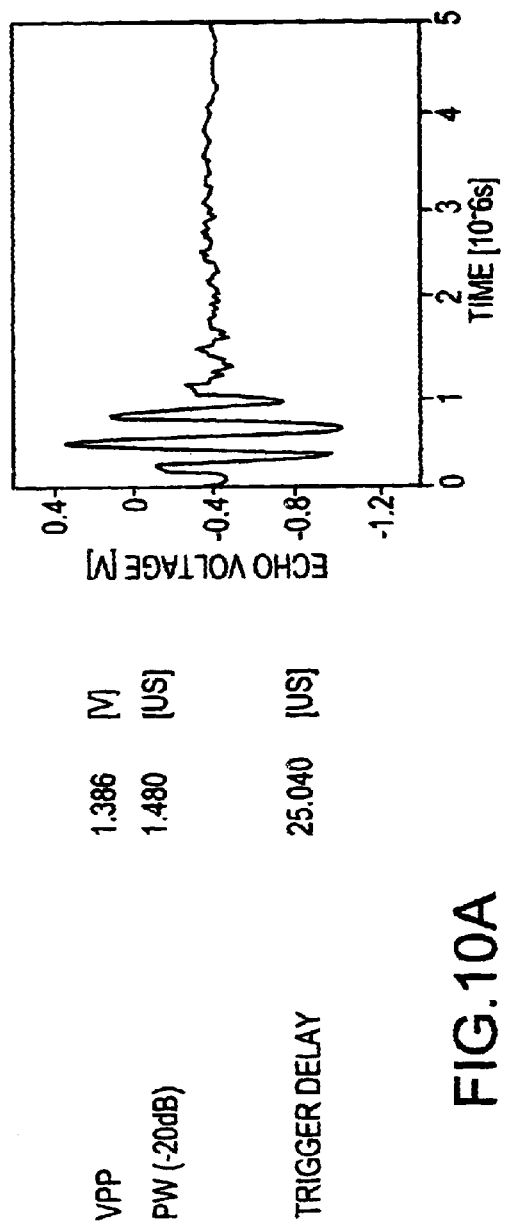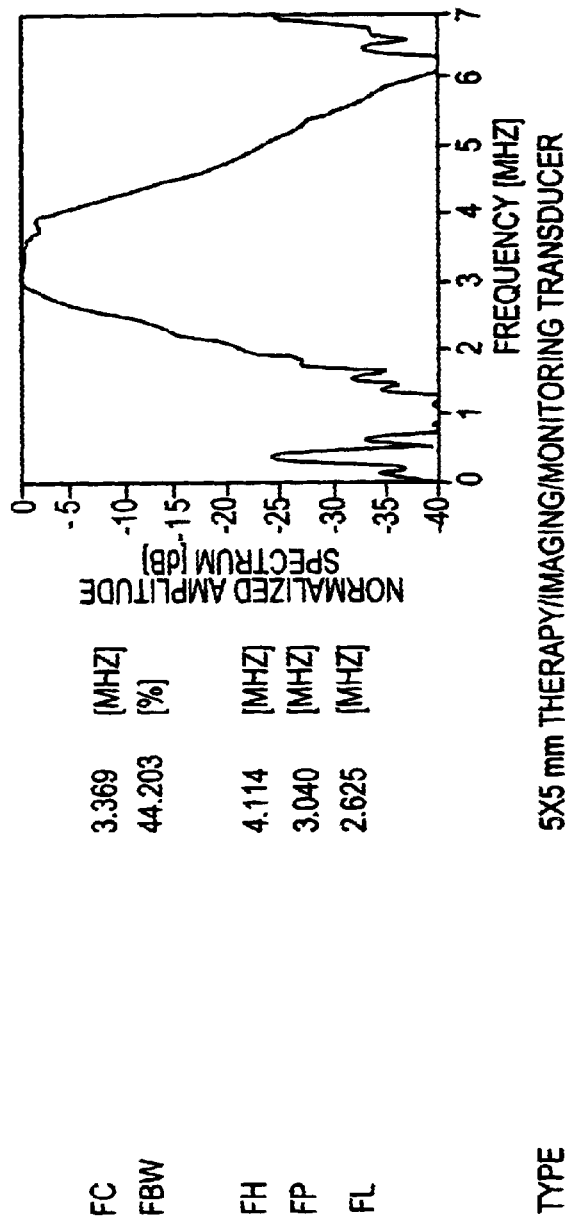
FIG. 10A
FIG. 10B

METHOD AND APPARATUS FOR SAFETY DELIVERING MEDICANTS TO A REGION OF TISSUE USING IMAGING, THERAPY AND TEMPERATURE MONITORING ULTRASONIC SYSTEM

CROSS REFERENCES TO RELATED APPLICATIONS

This is a continuation-in-part application of U.S. patent application Ser. No. 08/950,353, filed Oct. 14, 1997, now U.S. Pat. No. 6,050,943. Furthermore, this application claims priority to U.S. patent application Ser. No. 08/940,200, filed Oct. 3, 1997.

BACKGROUND OF THE INVENTION

1. Field of the Invention

This invention generally relates to a non-invasive therapeutic ultrasonic system, and more particularly, to a system which is capable of acoustically imaging and heating a certain region to be treated ("the treatment region") in target tissue for therapeutic purposes as well as acoustically monitoring the temperature profile of the treatment region. Further, the present invention relates to a method and apparatus for safely treating a region of body tissue using a single transducer and control unit to monitor and image a temperature profile of the tissue, and using the same transducer and control unit to melt a heat-activated, liposome encapsulated medicant disposed within the tissue.

2. Description of the Related Art

The absorption of energy in tissue, for example, in the human body produces an increase in temperature, which can be exploited for therapeutic purposes. The irradiation of ultrasound to the target tissue such as in the human body, which has been successfully used for decades mainly in increasingly sophisticated diagnostic imaging applications, also allows the target tissue to absorb a certain amount of energy. Thus, ultrasound may be used for therapeutic purposes.

Ultrasound encompasses any sound wave whose frequency is above the human hearing limit which is usually approximated at about 20 KHz. Since frequency and wavelength, and therefore resolution, are inversely related, the lowest sound frequency that is commonly used in imaging the human body is around 1 MHz with a constant trend toward higher frequencies in order to obtain better resolution. Weakening of ultrasonic signals increases with frequency in soft tissues.

In addition, ultrasonic energy at frequencies above 1.5 MHZ has an acoustic wavelength less than 1 mm in the human tissue. This energy is easily controlled in beamwidth and depth of penetration, and has a favorable absorption characteristic in the tissue. These aspects allow the energy to be precisely localized such that regions may be selectively heated while sparing overlying tissue structures.

Therefore, one must consider the exchange in benefits in the depth of penetration that must be achieved for a particular application of diagnostic imaging and the highest frequency that can be used. Applications that require deep penetration, such as cardiology and abdominal applications, typically use frequencies in the 2 to 5 MHz range. Others applications Such as ophthalmology and peripheral vascular applications require shallow penetration but high resolution. Frequencies up to around 20 MHz or higher are used for these types of applications.

Ultrasound has significant advantages for therapeutic applications as compared to micro-wave radio-frequency (RF) energy or optical energy (laser light). In contrast with ultrasound, RF energy is characterized by long wavelengths in tissue, with limited to poor control of energy deposition, and high absorption. These aspects of RF energy constrain its therapeutic usage for large superficial areas. On the other hand, the optical energy which is typically emitted from lasers can be precisely controlled in beamwidth, but the opacity and high absorption in tissue also limits its use to surface treatment or invasive procedures. Furthermore, laser and RF energy are emitted from ionizing radiation sources which are typically associated with some risk, unlike acoustic transducers which are typically used for generating ultrasound.

However, in contrast with the diagnostic uses, the therapeutic uses of ultrasound such as hyperthermia and non-invasive surgery have seen relatively little progress due to several technological barriers. The primary impediment has been a lack of the ability to monitor temperature in the treatment region during the therapeutic treatment process.

Specifically, one objective of the therapeutic application of ultrasound is to create a very well-placed thermal gradient in the target tissue to selectively destroy certain regions. For example, the hyperthermia technique typically requires maintaining tissue temperature near about 43 degrees Celsius, while the goal of non-invasive surgery is typically to elevate tissue temperature above and beyond about 55 degrees Celsius. Moreover, during the therapeutic treatment process, the physiological response of the target tissue is directly related to the spatial extent and temporal duration of the heating pattern. Consequently, in order to appropriately perform feedback and control of the therapeutic treatment process for obtaining successful results, it is absolutely essential to monitor the temperature in the target tissue, for example, so as to know whether or not the temperature in the treatment region has been raised to a level that produces a desired therapeutic effect or destruction in the tissue. In addition, it is preferable to know the temperature distribution in the treatment region and its vicinity for enhancing therapeutic effect.

In the conventional technique, the therapeutic ultrasonic system has typically relied upon thermocouple probes for monitoring the temperature in the treatment region and the vicinity thereof. However, the thermocouple probes are highly invasive because they have to be inserted into the region-of-interest. In addition, use of the thermocouple probes has necessarily led to very poor spatial resolution since only a small number of probes could be safely embedded in the region-of-interest. Furthermore, the embedded thermocouple probes are likely to disturb the acoustic propagation in the tissue and typically cause excessive heating at the probe interface during the therapeutic treatment process. This results in an undesirably modified temperature distribution as well as erroneous measurements.

Another factor which has curtailed progress in the therapeutic uses of ultrasound has been the design of the conventional acoustic transducers.

In general, for the therapeutic treatment process, imaging of the treatment region is necessary to determine the location of the treatment region with respect to the acoustic transducers as well as to evaluate progress of the treatment process. Such essential functions of imaging as well as the aforementioned temperature monitoring may be implemented with the same acoustic transducer to be used for therapeutic purposes, since the acoustic transducers can actually produce an image of the region-of-interest by employing well-established imaging techniques such as B-scan imaging. However, the conventional acoustic transducers which are typically employed for therapeutic purposes are acoustically large, often single-element devices having narrow bandwidth in the frequency domain. Although they are designed to efficiently transmit acoustic energy to the target tissue, the conventional acoustic transducers are typically unsuited for imaging of the treatment region and/or monitoring the temperature profile therein. This precludes development and implementation of these vital functions for performing a desirable precise therapeutic treatment process.

Some prior art references teach the use of ultrasound for therapeutic purposes. For example, U.S. Pat. No. 4,757,820 to Itoh discloses an ultrasound therapy system having functions of imaging and heating the target using ultrasound beams for therapeutic purposes. The system disclosed therein, however, does not include temperature monitoring of the target tissue (treatment region).

U.S. Pat. No. 5,370,121 to Reichenberger et al. discloses a method and apparatus for non-invasive measurement of a temperature change in a subject, in particular a living subject, using ultrasound waveforms. The method and apparatus disclosed therein, however, relies on a differential ultrasound image between two successive ultrasound images of the target. In other words, any temperature change is detected as a temperature-induced change in brightness between the two images, which appears in the differential image. Consequently, an actual real-time monitoring of the temperature may be difficult in the disclosed method and apparatus. Moreover, although the method and apparatus can detect changes in the temperature of the target, an absolute value of the target temperature may not be obtained therefrom. In addition, any movement of the target may introduce changes in the differential image, which may cause erroneous results.

Furthermore, although it is not distinctly intended to be applied in the therapeutic treatment process for a target tissue such as in the human body, U.S. Pat. No. 5,360,268 to Hayashi et al. discloses an ultrasonic temperature measuring apparatus in which a temperature of the target medium is calculated using a propagation time of ultrasonic waves which propagated for a predetermined distance in the target medium. The apparatus disclosed therein, however, is mainly described as employing separate ultrasonic elements which respectively function for a transmitter and a receiver of the ultrasonic waves.

While some prior art temperature monitoring techniques exist, see, for example, U.S. Pat. No. 4,807,633 issued to Fry on Feb. 28, 1989, such techniques are complex and have limited applicability. That is, use of such techniques essentially preclude use of the system for purposes of imaging, unless one were to use multiple transducers. In that regard, while two or more physically separated transducers can be used to accomplish imaging and therapy, typically with one configured for imaging and the other for therapy, such a-system is susceptible to the generation of imprecise data and is overly complex and expensive.

Other prior art references have discussed methods for using ultrasound therapy to treat biological tissues. For example, U.S. Pat. No. 5,149,319 issued to Linger discloses a method for heat treating biological tissues which includes administering a therapeutically effective amount of a hyperthermic potentiator to the tissue and then applying ultrasound to heat the tissue to a temperature of at least about 43 degrees C. Although the potentiators disclosed in this method result in making the hyperthermic ultrasound a more selective and more effective therapeutic method for treating tissue, there is no inclusion of a monitoring means to safeguard against potential overheating and its resulting tissue damage. Further, it should be noted that the hyperthermic potentiators are used to increase the acoustic heterogeneity and generate cavitation nuclei in tumors and tissues, and that this cavitation effect can be harmful to the tissue.

Still other patents disclose the use of lipid-coated micro bubbles or liposomes with ultrasound energy to control and enhance the therapeutic effect on the tissue. For example, U.S. Pat. No. 5,215,680 issued to D'Arrigo discloses an embodiment of the invention which utilizes liposomes which have pooled at the tumor site to enhance the known cavitational and heating effects of ultrasound. The D'Arrigo method involves intravenously injecting liposomes into the body such that they pool at a predetermined area which was previously identified by ultrasonic imaging and then intensifying the ultrasound signal to provide a therapeutic heating and/or cavitational effect. This method also fails to provide means for monitoring the temperature of tissue in order to prevent tissue damage that can occur from overheating.

U.S. Pat. No. 5,348,016 issued to Unger discloses the use of contrast agents for ultrasonic imaging which comprise gas filled liposomes. This patent reference also suggests using liposomes as hyperthermic potentiators for ultrasound and as drug delivery vehicles for use with ultrasound. More specifically, another patent issued to Unger et al., U.S. Pat. No. 5,580,575, discloses a therapeutic drug delivery system using gas-filled micro spheres which includes a method for the controlled delivery of therapeutic compounds to a region comprising the steps of (i) administering the gas-filled micro spheres containing a drug into a patient, (ii) monitoring the micro spheres using ultrasound to determine the presence of the micro spheres in the region, and (iii) rupturing the micro spheres using ultrasound to release the drug in that region. Although these references disclose the use of ultrasound therapy with drug containing liposomes to effect the treatment of tissue, these references do not disclose the use of imaging and temperature monitoring functions to facilitate treatment planning and feedback to ensure the safe treatment of the tissue. Further, these references do not disclose heat treatment of the liposomes themselves, nor the use of heat sensitive liposomes.

Thus, it would be advantageous to provide a compact, non-invasive system capable of acoustically performing the therapeutic heating and imaging of the treatment region in a target tissue as well as temperature monitoring in the treatment region with a single acoustic transducer.

Further, the use of drug or medicant containing liposomes to enhance the therapeutic treatment of targeted areas within the body has become preferred for certain types of medical disorders. Accordingly, there is a need for an ultrasound activated therapy system using medicant containing liposomes which incorporates image and temperature monitoring to assure the safe therapeutic treatment of bodily tissue.

SUMMARY OF THE INVENTION

In accordance with various aspects of the present invention, a non-invasive therapeutic ultrasonic system is provided, which features a single acoustic transducer and some other subsystems capable of acoustically performing therapeutic heating and imaging of the treatment region as well as acoustically monitoring the temperature profile in the treatment region and the vicinity thereof. Also disclosed herein is a system architecture and associated components as well as algorithms which can be implemented to acoustically achieve the heating, imaging, and temperature monitoring functions. The imaging and monitoring functions allow precise feedback and control of the therapeutic treatment process so that the therapy can be conducted more successfully. In addition, because a single transducer is utilized, perfect correspondence is obtained; that is, image artifacts and/or imprecise registration difficulties yielded through use of multiple transducers can be avoided.

A novel acoustic transducer disclosed herein is capable of generating high acoustic power for the therapeutic treatment process, while at the same time providing a good imaging function. Specifically, in order to obtain good lateral resolution in the imaging process, the acoustic transducer of the present invention is preferably divided into an array of sub-elements each processing acoustic waves with a sufficient bandwidth for good axial resolution in the imaging process.

These imaging requirements are also extended to the acoustic temperature monitoring function of the treatment region. In accordance with various aspects of the present invention, an acoustic temperature measurement subsystem disclosed herein is capable of non-invasively mapping the temperature distribution or profile in the target tissue in real-time. This feature is accomplished by measuring the time-of-flight and amplitude data of acoustic pulses through the region-of-interest while exploiting the temperature dependence of the speed of sound and acoustic attenuation in the target tissue. The acoustic nature of this process allows the same acoustic transducer which is used for the imaging and therapy functions to be used for the real-time temperature monitoring function. Alternatively, the use of multiple acoustic transducers allows the temperature mapping to be conducted with a higher spatial resolution. The valuable information gathered on the temperature in the target tissue can be used to achieve precise control of the spatial distribution of heating, provide detailed knowledge of the heating duration, and provide quantitative temperature data during the therapeutic treatment process, which has not been previously possible in the conventional art.

In accordance with another aspect of the present invention, a method and apparatus is provided for the safe delivery of medicants within the body using ultrasonic energy. Further, an ultrasound-activated therapy system is provided which utilizes thermally-sensitive liposomes that dissolve upon heating with ultrasound, thereby releasing any drugs or medicants contained within the liposomes at predetermined temperatures into the body for therapeutic treatment. In addition, a method and apparatus is provided for delivering medicant containing liposomes within bodily tissue using ultrasound which incorporate image and temperature monitoring means to assure the proper delivery of the medicant and the safe therapeutic treatment of bodily tissue. Still further, an apparatus is provided for safely delivering a medicant to a region of body tissue which utilizes a single or multiple transducer for monitoring a temperature profile of the tissue region and heating a thermosensitive medicant containing liposome contained in the tissue region.

Additionally, an efficient method and apparatus is provided for safely delivering a medicant to a tissue region which utilizes a single transducer for imaging, temperature monitoring and therapy.

The aspect of the invention directed toward a method for safely delivering a medicant to a tissue region includes the steps of administering a thermosensitive liposome encapsulated medicant to a region of tissue in a body, locating the tissue region using ultrasound imaging, applying ultrasound therapy to heat the tissue region, monitoring the temperature of the tissue region using ultrasound imaging to create a temperature profile, and alternating application of ultrasound imaging and ultrasound therapy until a temperature threshold is reached. The temperature of the tissue region is continuously determined to generate a temperature profile. The temperature profile is continuously and ultrasonically controlled by heating the tissue region to a temperature less than 44 degrees C. and greater than the melt temperature of the liposome. The melt temperature of the liposome is greater than the body temperature of the body including the tissue region. The "melt temperature" is defined as the temperature where the liposome undergoes phase transition from a crystalline to a liquid or gel.

Preferably, the tissue region is heated to a temperature of about 40–43 degrees C. Typically, the body-temperature is about 37–38 degrees C. The recitation "about" is intended to include temperatures proximate to the recited point or range of temperatures; whereby the present invention would operate in an equivalent manner to one of ordinary skill in the art, or such proximate temperatures would be interchangeable with the recited temperature to one of ordinary skill in the art. Moreover, the melt temperature of the liposome is very sensitive having a variance of about plus or minus 0.5 degrees C., e.g., between 0.1 degrees C. and 0.9 degrees C.

Preferably, the medicant is a therapeutic drug, a reagent, or a bioactive compound.

In addition, the medicant can also be one or more medicants, such as, for example, two different liposomes. Once the liposome melts, it may act as a carrier across cell membranes.

The aspect of the invention directed toward an apparatus for safely delivering a medicant to a tissue region includes means for continuously determining a temperature profile of the tissue region, ultrasonic means for continuously monitoring the temperature of the tissue region and heating a thermosensitive liposome encapsulated medicant located within the tissue region, and means for driving the monitoring and heating means.

The monitoring and heating means are preferably a single transducer that is capable of heating the tissue region to a temperature greater than the melt temperature of the liposome which is greater than the body temperature of the body containing the tissue region. The transducer heats the tissue region with high spatial resolution. The apparatus may also include means for displaying the temperature profile. The means for displaying the temperature profile may be a visual display terminal. Further, the means for continuously determining the temperature profile of the tissue region may be a control unit. The means for driving the transducer may also be the control unit.

These and other objects, features and advantages of the present invention will become more apparent to those skilled in the art from the following more detailed description, by way of nonlimitative example, of various particular embodiments of the invention taken with reference to the accompanying drawings.

BRIEF DESCRIPTION OF THE DRAWINGS FIGURES

Preferred exemplary embodiments of the present invention are described in conjunction with the appended drawing figures in which like numerals denote like elements, and:

Figure 5:
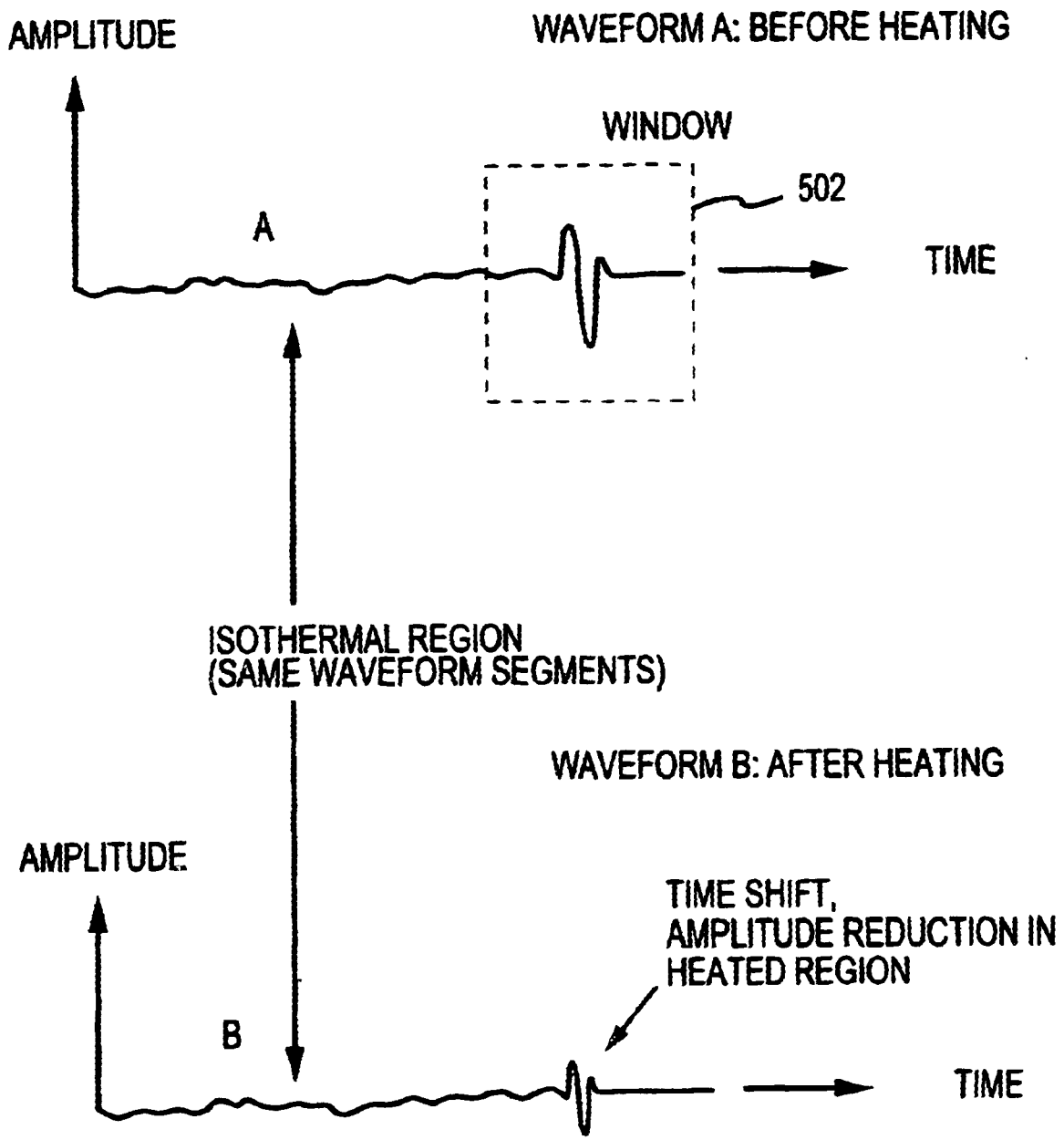
Figure 6:
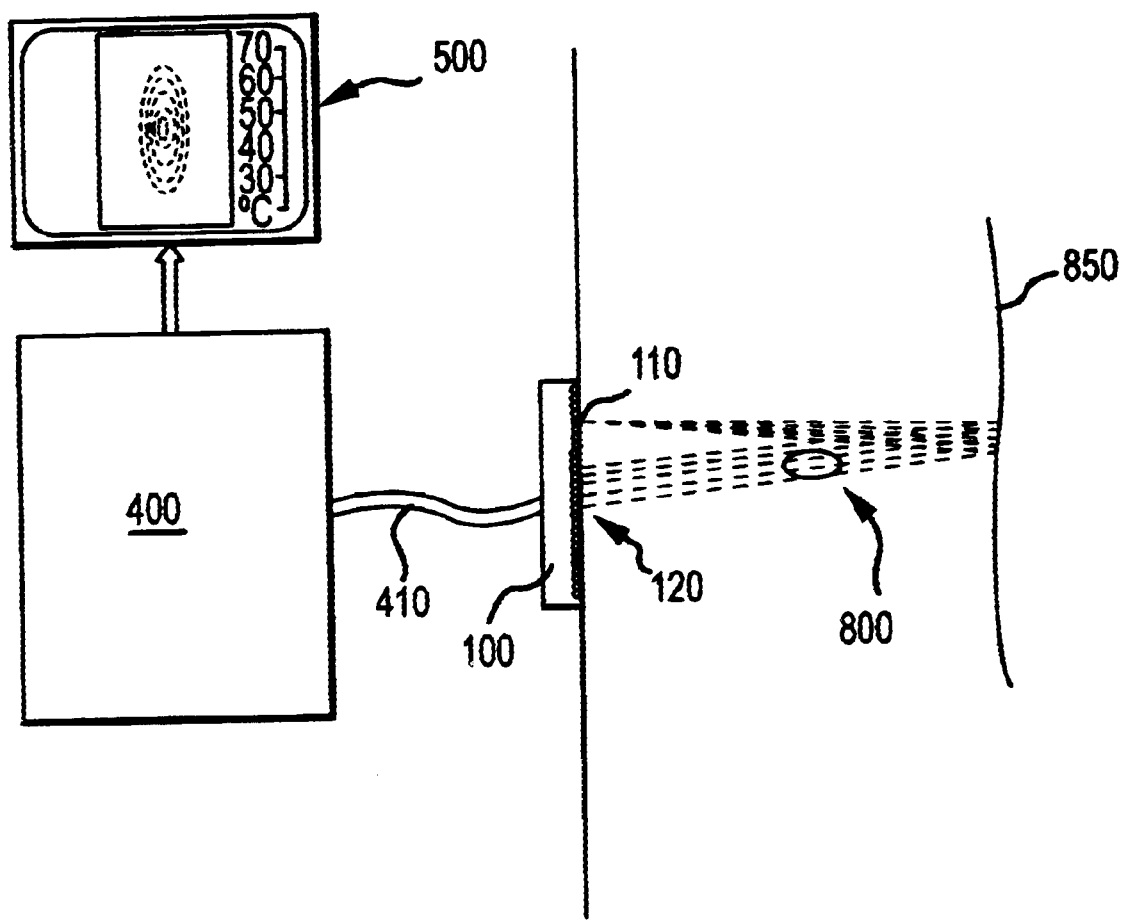

FIG. 5 depicts waveforms of heated and unheated states illustrating the time shift and amplitude change of the echo in the region of interest as well as one method for the acoustical monitoring of the spatial and temporal distribution of temperature in a tissue region treated with the apparatus of the present invention wherein ultrasound echo waveforms before and after tissue heating are compared for time shifts and amplitude variations in the heated region;

FIG. 6 is a diagram of a further embodiment of a temperature monitoring subsystem interfaced to the acoustic transducer assembly according to the present invention.

Figure 7:
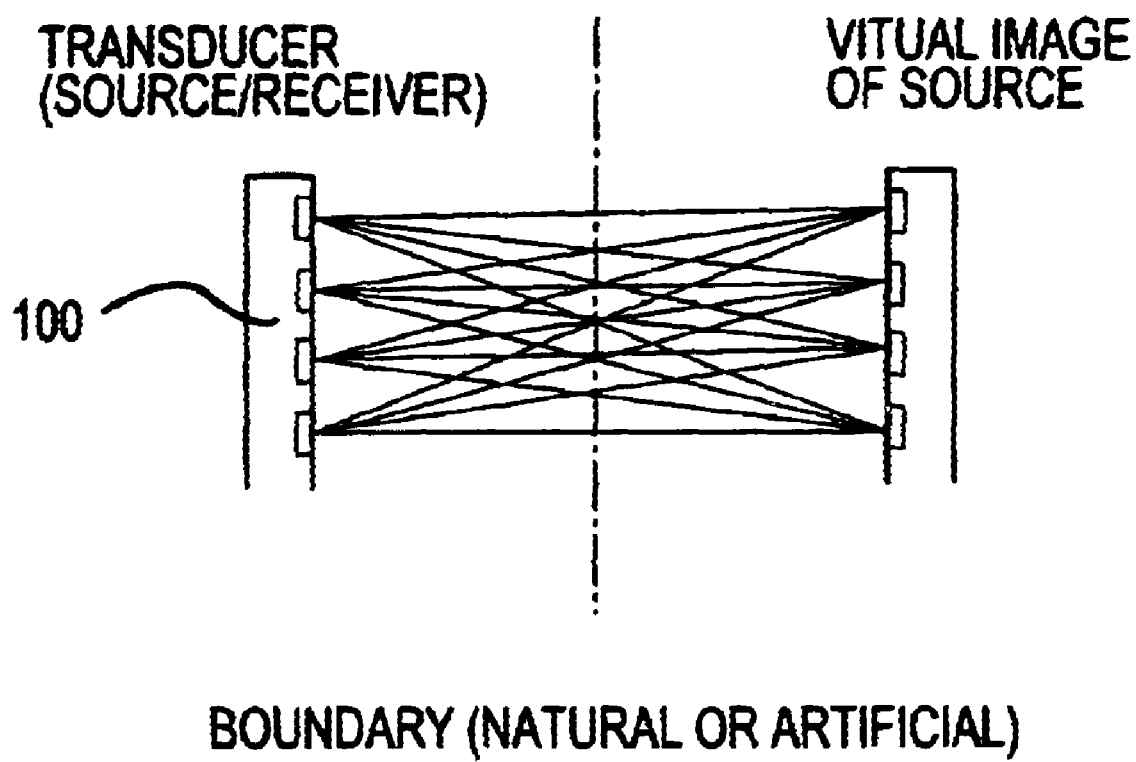
Figure 8:
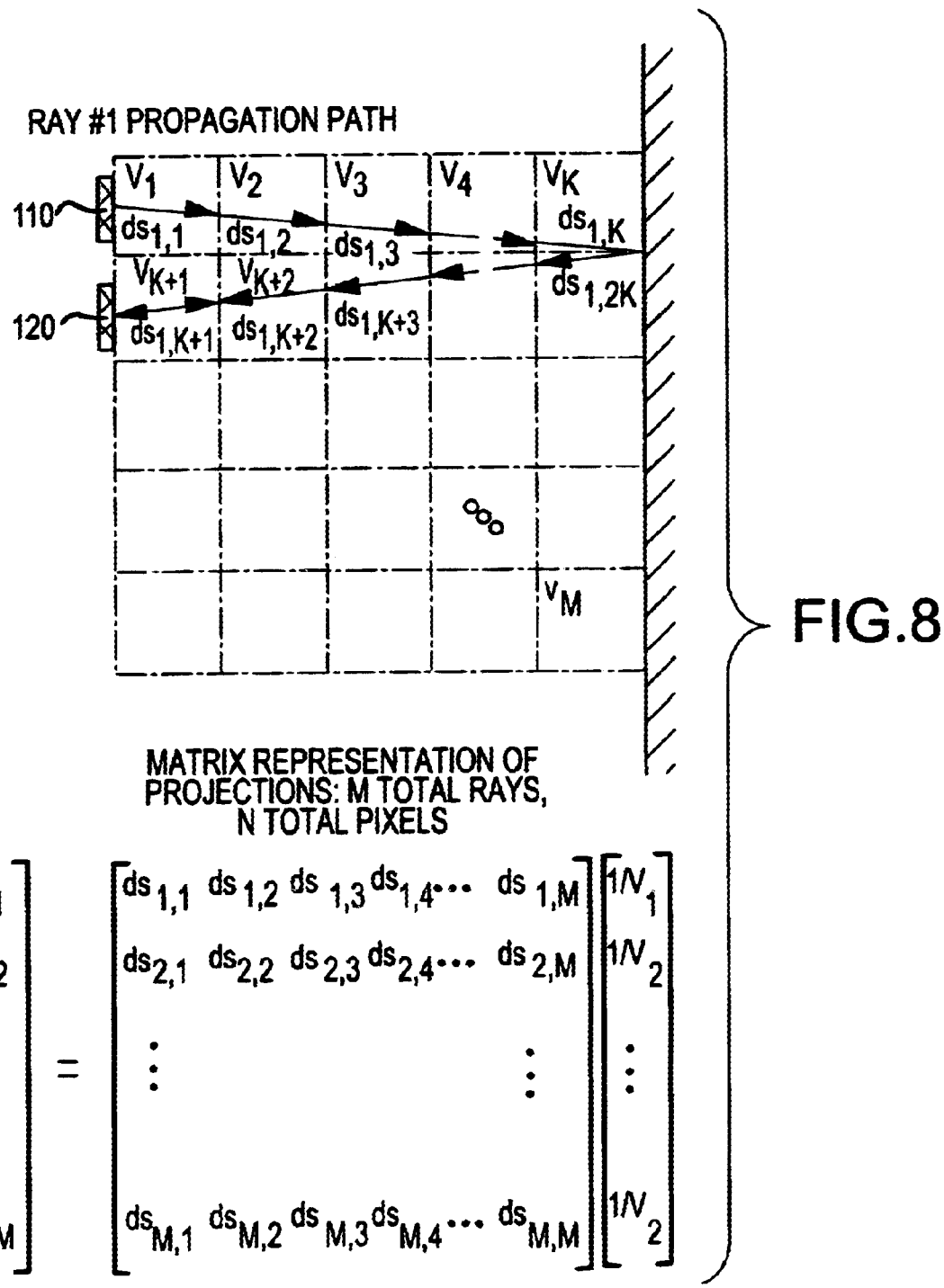
Figure 11A:
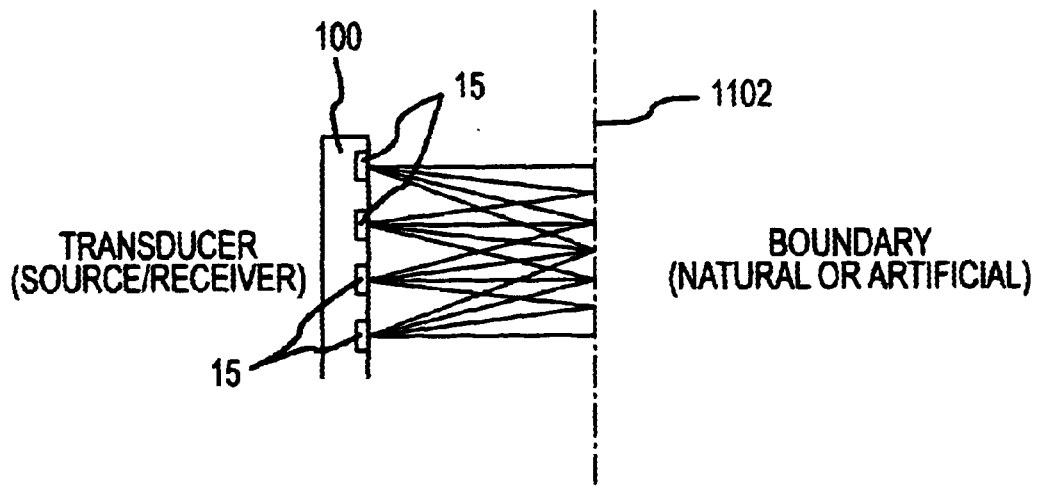
Figure 11B:
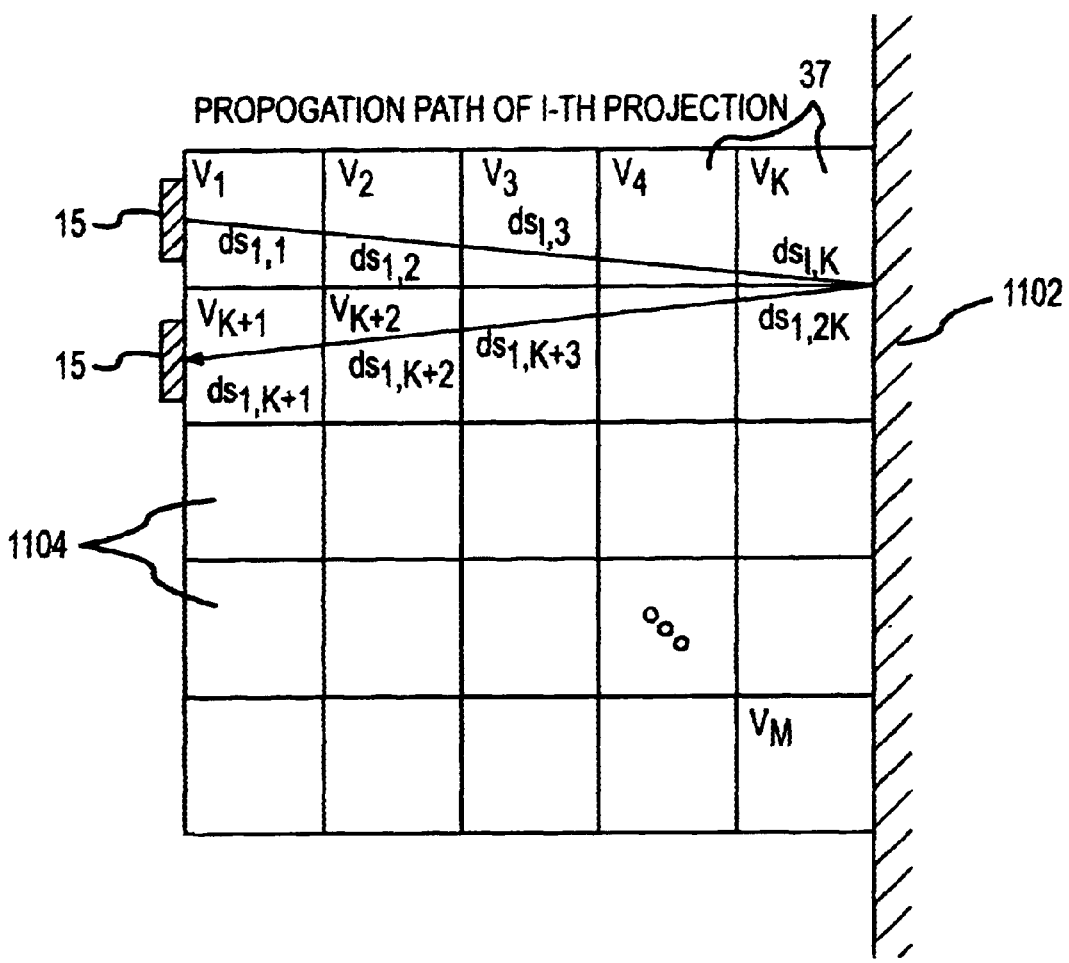
Figure 12:
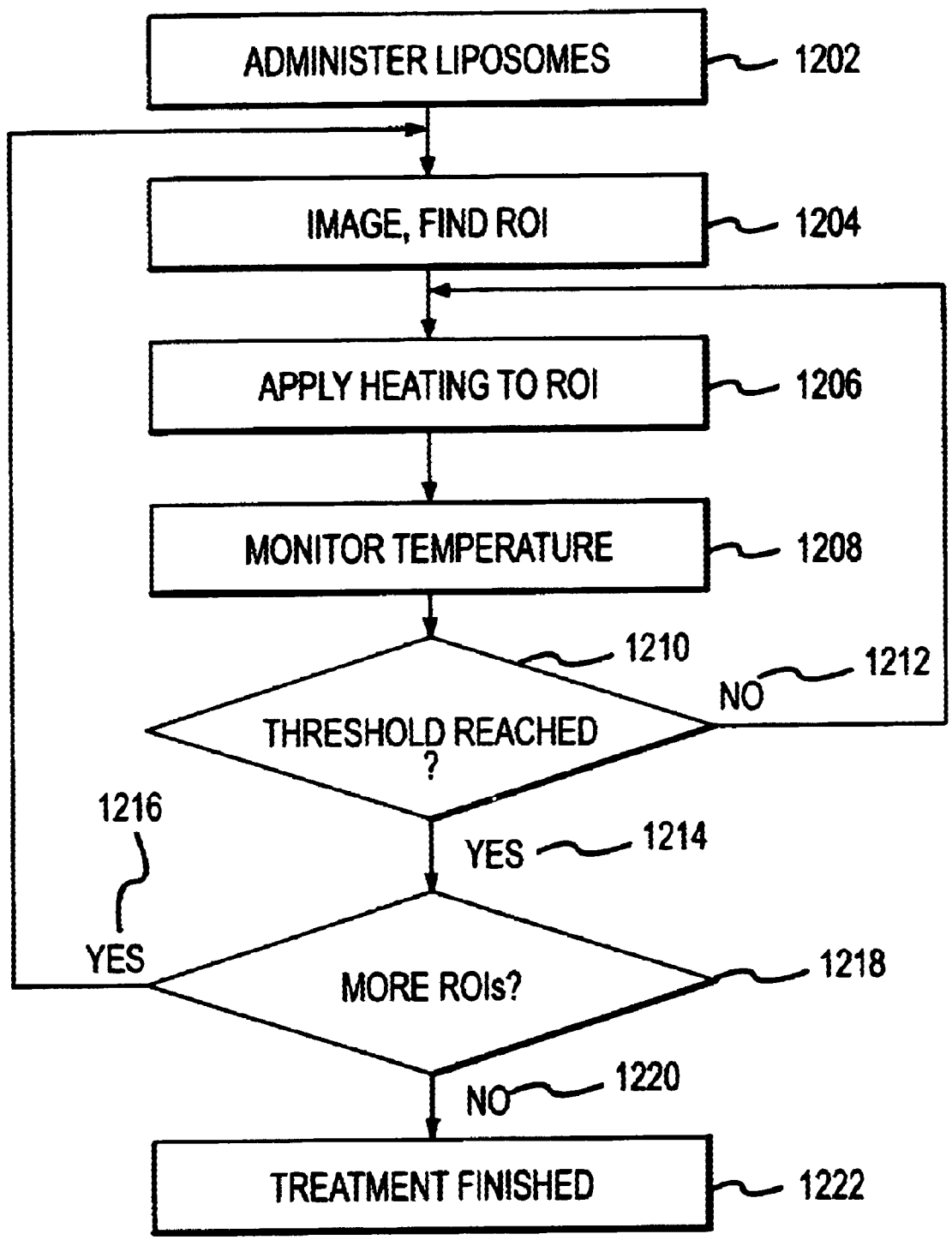

FIG. 7 is a depiction of the intersecting paths of acoustic rays possible from a transducer source;

FIG. 8 illustrates a tomographic configuration useful in connection with yet another embodiment of a temperature monitoring subsystem according to the present invention;

FIGS. 9A–D show the characteristics of an exemplary transducer made in accordance with various aspects of the present invention;

FIGS. 10A–B show, respectively, the pulse echo waveform and the frequency spectrum of the echo of an exemplary transducer made in accordance with various aspects of the present invention;

FIG. 11 is a schematic drawing showing another method for acoustically monitoring the spacial and temporal distribution of temperature in a tissue region treated with the apparatus to the present invention when a natural or artificial boundary is used to reflect a myriad of sound waves back to the transducer after crossing the treatment region; and FIG. 12 is a flowchart illustrating the method of the present invention for safely delivering encapsulated medicants to a tissue region using ultrasound.

DESCRIPTION OF THE PREFERRED EXEMPLARY EMBODIMENTS

A system for achieving successful ultrasonic therapy procedures in accordance with the present invention includes four major subsystems or components. Specifically, they are an acoustic transducer assembly, an imaging subsystem, a therapy subsystem (also referred to as a "therapeutic heating subsystem"), and a temperature monitoring subsystem, which are illustrated in FIGS. 1 through 4, respectively. Although not shown in the drawing figures, the system further includes components typically associated with a therapy system, such as any required power sources, memory requirements, system control electronics, and the like.

Figure 1:
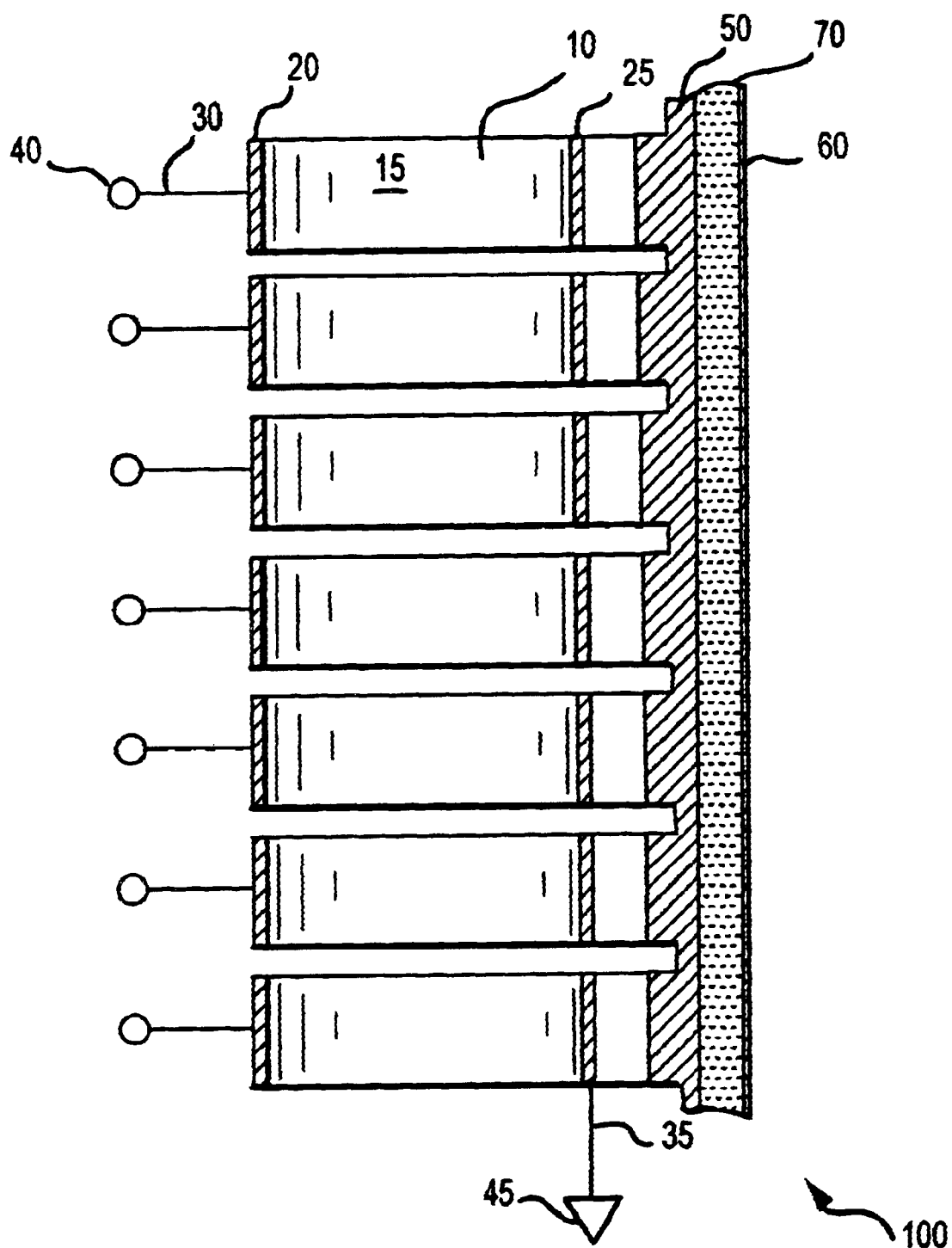
FIG. 1 is a cross-sectional view of an acoustic transducer assembly according to the present invention.

With reference to FIG. 1, the acoustic transducer assembly 100 included in the system of the present invention will be described in detail below. As shown in the cross-sectional view of FIG. 1, the acoustic transducer assembly 100 includes a piezoelectric ceramic plate 10. The air-backed side of the ceramic plate 10 may be partially diced to have a plurality of curved (e.g. concave) portions 15 to form a linear array structure. The thickness of the diced ceramic plate is selected to provide a center frequency for example from 500 kHz to 20 MHZ, with lower frequencies yielding deeper penetration and higher frequencies providing greater resolution. The concave portions 15 constituting the transducer array are spaced to achieve good lateral resolution in the imaging function. On the face of each of the concave portions 15, a metal electrode 20 is provided to connect the ceramic plate 10 to the system control electronics (not shown in the figure) via a cable 30 and a terminal 40. The other face of the ceramic plate 10 is configured such as to receive a common metal electrode 25. The common electrode 25 is also connected to the system control electronics via a cable 35 and a terminal 45.

In addition, although a concave portion is described above, it should also be noted that portion 15 may also comprise a substantially flat configuration with a natural focus arrangement, e.g., without a focusing lens. Moreover, portion 15 can also be configured with a substantially flat configuration having a convex or concave lens arrangement. Accordingly, portion 15 may be configured in various manners without departing from the scope of the present invention.

The phrase "air-backed" means that there is no backing material provided on the back side of the acoustic transducer assembly 100, unlike the typical conventional acoustic transducers. Specifically, the conventional acoustic transducers are typically provided with some kind of backing layer typically made of a loaded epoxy, such as an alumina powder epoxy. The loaded particles in the backing layer, however, introduce increased acoustic impedance and provide scattering surfaces therein. Accordingly, when the generated acoustic waves come to the backing layer and hit the loaded particles included therein, the particles tend to disburse the acoustic waves in different directions into the epoxy matrix so that attenuation increases. As a result, the operational efficiency of the acoustic transducer decreases since some portion of the generated acoustic energy is absorbed in the backing layer. On the other hand, in the acoustic transducer assembly 100 of the present invention, by providing no backing layer on the back end of the ceramic plate 10, the acoustic waves are reflected without being absorbed there to propagate toward the target tissue, resulting in the increased efficiency.

Alternatively, a certain backing layer may be provided as long as it has a very low acoustic absorption so that any significant absorption of the generated acoustic energy does not happen.

On the common electrode 25, one or more acoustic matching layers 50 is bonded using an adhesive Such as an epoxy. When a loaded epoxy is used as the adhesive, the acoustic matching layer 50 can be simply cast thereon since they adhere naturally to each other. The acoustic matching layer 50 is intended to obtain appropriate impedance matching between the ceramic plate 10 and the target tissue. Consequently, efficient transfer of acoustic power from the ceramic plate 10 to the target tissue can be maintained to achieve an appropriate temperature increase in the target tissue, resulting in desired therapeutic results. When the acoustic matching layer 50 (or layers) is bonded to the ceramic plate 10 (precisely, to the common electrode 25) with a loaded epoxy, the acoustic impedance can be easily adjusted by changing the amount of metal particles loaded in the epoxy.

At the same time, acoustic matching layer(s) 50 can increase the bandwidth of the emitted acoustic waves in the frequency domain. This aspect is suitable for the effective imaging function.

Specifically, in order to improve the sensitivity in the imaging function, it is preferable that the emitted acoustic waves are very pulsive in the time domain since acoustic pulses with a very short pulse width can produce clearly distinct echoes from different interfaces existing in the target tissue. The shorter the width of the acoustic pulses, the more clearly the distinct echoes can be resolved, thereby resulting in improved resolution in the obtained images. The short pulse in the time domain means a wide range in the frequency domain which covers a large spectrum. On the other hand, however, when considering an efficient transmission of the acoustic energy from the acoustic transducer assembly 100 to the target tissue, which is important for the therapeutic treatment process, it is preferable to use stable acoustic waves such as "continuous waves" or gated bursts, which in turn means that the bandwidth thereof in the frequency domain is narrow. Thus, trade-off between the efficiency in the therapeutic function and the sensitivity in the imaging function has to be satisfied by appropriately setting the bandwidth of the acoustic waves to be emitted.

Without acoustic matching layer(s) 50, the bandwidth of the emitted acoustic waves is mainly based on the design of the ceramic plate 10 which actually generates the acoustic waves. This results in limited degrees of freedom for adjusting the bandwidth. Providing one or more acoustic matching layer(s) 50 makes it possible to properly adjust the bandwidth in a wide range without substantially changing the design of the ceramic plate 10.

Typically, the thickness of the acoustic matching layer 50 is set to be on the order of a quarter of a wavelength of the acoustic waves. In addition, it is preferable that the acoustic impedance of the acoustic matching layer 50 be set to be approximately equal to the square root of the acoustic impedance of the ceramic plate 10, times the acoustic impedance of the target tissue or, more preferably, the acoustic impedance of the ceramic plate raised to the $\frac{1}{3}$ power, times the acoustic impedance of the target tissue raised to the $\frac{2}{3}$ power. Also, multiple matching layers may be used, of course, with suitable changes in layer impedances.

The acoustic matching layer 50 can be made of various types of materials, such as ceramics, plastics, metals and composite materials thereof. Preferably the matching layer may exhibit good thermal conductivity and low acoustic attenuation. Matching layer (or layers) 50 may be cut or diced, such as shown on FIG. 1, to maintain high acoustic isolation, i.e., low acoustic crosstalk. However, any heating of the matching layer(s) of ceramic may be controlled via the duty cycle of the drive signal or via active or passive cooling methodologies. In addition, any other conventional cooling technique and/or methodology may be utilized.

Although not shown on FIG. 1, it should be appreciated that transducer assembly 100 may be provided with a back layer (not shown) suitably configured to modify the bandwidth of the transducer and/or serve as a heat sink.

The ceramic plate 10 and other related components configured as set forth above are coupled to the target tissue via a fluid 70 circulating between the acoustic matching layer 50 and an acoustically-transparent membrane 60. The fluid 70 also functions as a coolant for the ceramic plate 10 and the acoustic matching layer 50 and may also aid in controlling the temperature of the tissue at the interface. Temperature control via a circulating fluid, thermoelectric cooling module and/or pneumatic or other devices may also be utilized in accordance with various aspects of the present invention. Furthermore, the acoustic transducer assembly 100 having the aforementioned configuration is enclosed in a water-tight housing (not shown in the figure).

The circulating fluid 70 has two major functions as mentioned above. One of them is to couple the ceramic plate 10 and the acoustic matching layer 50 to the target tissue. The other is to remove the waste heat away from the acoustic transducer assembly 100. In particular, the energy conversion efficiency of the acoustic transducer assembly 100 is typically about 80%, and consequently, some portion of the input electrical power becomes the waste heat. When a large amount of electrical power is input to the acoustic transducer assembly 100, the assembly 100 is heated up. This may result in reduced efficiency and altered operational characteristics, which are likely to produce adverse effects on the therapeutic purposes. The circulating fluid 70 therefore keeps the acoustic transducer assembly 100 at a stable and constant temperature by cooling it off.

The fluid 70 is typically water. Alternatively, any suitable mineral oil, plant oil, or other suitable liquid could be used as the fluid 70.

Figure 2:
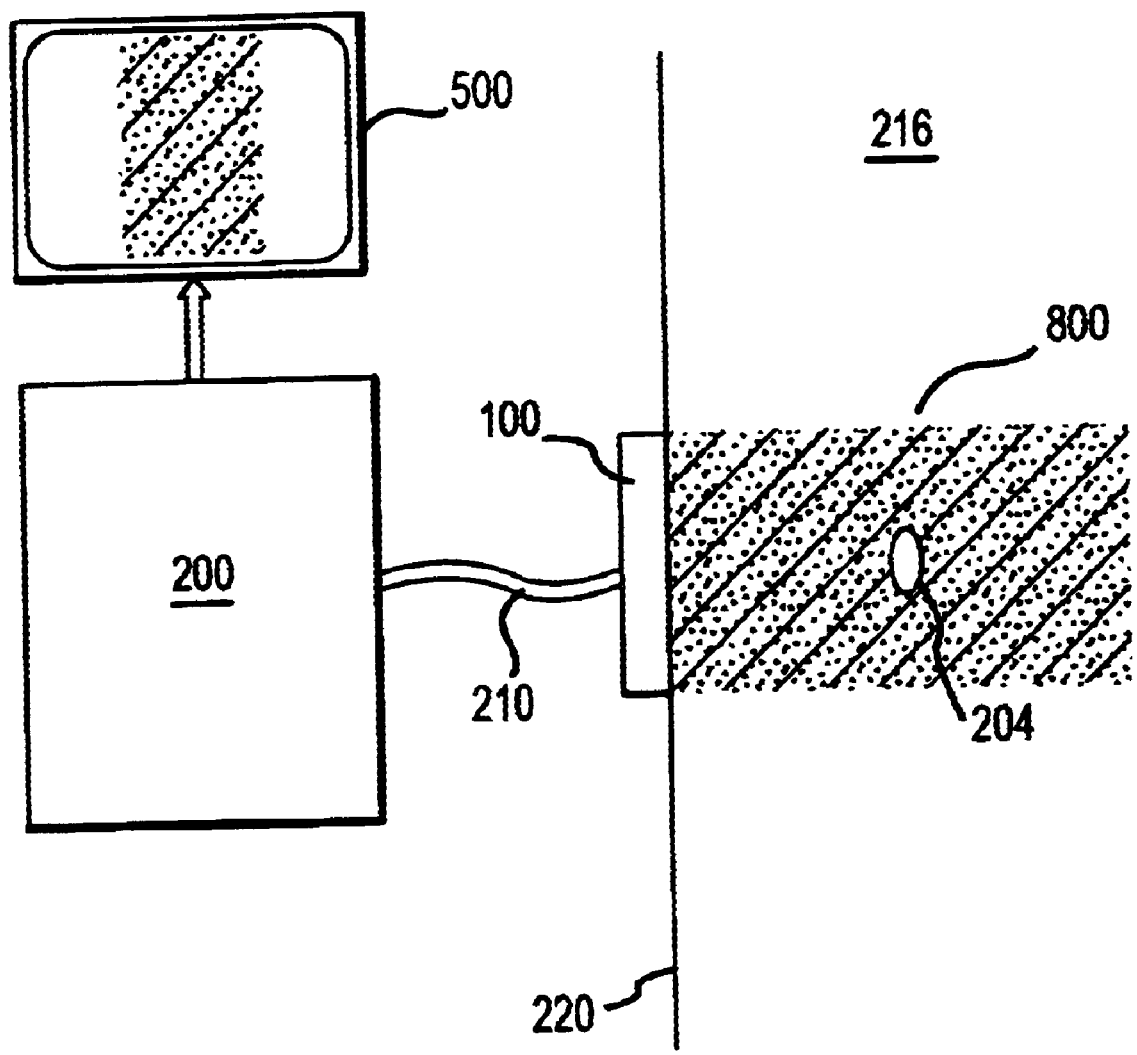
FIG. 2 is a diagram of an imaging subsystem interfaced to the acoustic transducer assembly according to the present invention.

With reference to FIG. 2, an imaging subsystem 200 which is interfaced to the acoustic transducer assembly 100 is described below. The imaging subsystem 200 connected to the acoustic transducer assembly 100 via a cable 210 includes a beam forming control unit. The unit is operated so that the acoustic transducer assembly 100 scans the region-of-interest, including the treatment region, in the target tissue 800 with the acoustic waves. The returning acoustic signal is received by the acoustic transducer assembly 100, and then sent to the imaging subsystem 200 to generate ultrasonic images of the treatment region. The thus generated image is displayed on a video display terminal 500 to assist the user in appropriately positioning the acoustic transducer assembly 100 with respect to the treatment region in the target tissue 800 prior to actually commencing the therapeutic treatment process.

Figure 3:
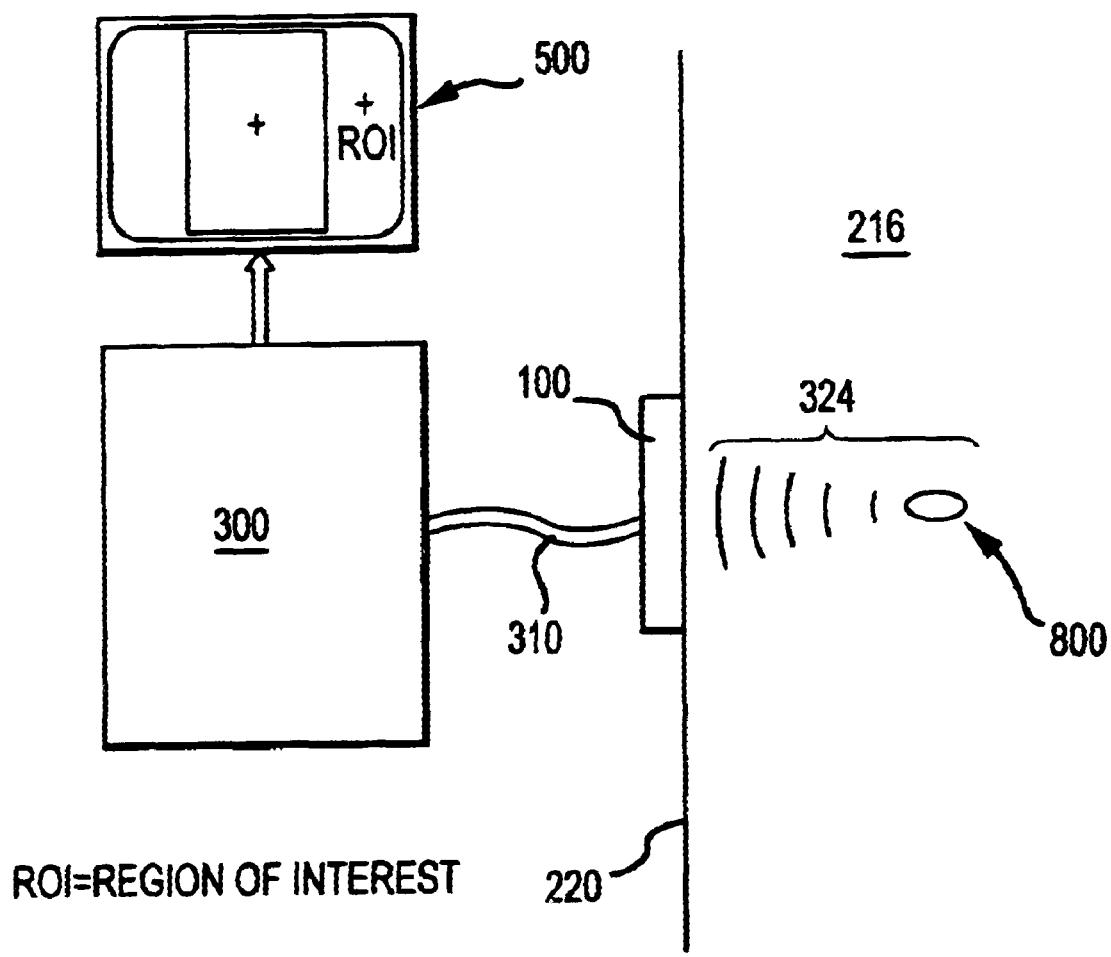
FIG. 3 is a diagram of a therapy subsystem interfaced to the acoustic transducer assembly according to the present invention.

With reference to FIG. 3, a therapy subsystem (a therapeutic heating system) 300 which is interfaced to the acoustic transducer assembly 100 is described below.

The therapy subsystem 300 connected to the acoustic transducer assembly 100 via a cable 310 includes power RF drivers which are interfaced to the linear array of the acoustic transducer assembly 100, i.e., to each of the respective portions 15 of the ceramic plate 10 shown in FIG. 1. The power RF drivers are also connected to the common electrode 25 provided on the other face of the ceramic plate 10. By appropriately applying RF signal voltages to the ceramic plate 10 from the connected power RF drivers, high power acoustic energy is generated. The drivers are controlled in-time so that the acoustic transducer assembly 100 transmits, steers, and/or focuses the acoustic waves to the region-of-interest including the treatment region in the target tissue 800. Heating power and heating time as well as transducer anodization are all controlled during the therapeutic treatment process to achieve the proper heating pattern and therapeutic dosage. The control can be supplemented by the feedback of information from the temperature monitoring subsystem described later.

In connection with yet another embodiment of the present invention, temperatures are monitored in a manner calculated to avoid tissue motion artifacts. For example, in the case where a localized region is heated, in accordance with this embodiment of the present invention, the heated region is interrogated with a pulse echo signal substantially immediately thereafter. In such a case the echo from the heated region will be changed in time and amplitude. For example, the acoustic attenuation in tissue approximately doubles from 50° C. to 70° C. Preferably, the region is measured immediately before and after heating and thus, tissue motion artifacts are avoided, as well as any acoustic propagation effects.

In the case where only a small region is treated at a time, an isothermal region about the hot spot is engendered. Therefore, the time-of-flight and the amplitude of wave incident on the heated region is the same before and after the therapeutic energy is delivered. Thus, the amplitude change and time change measured after therapy will be due substantially to the tissue treated.

Figure 4:
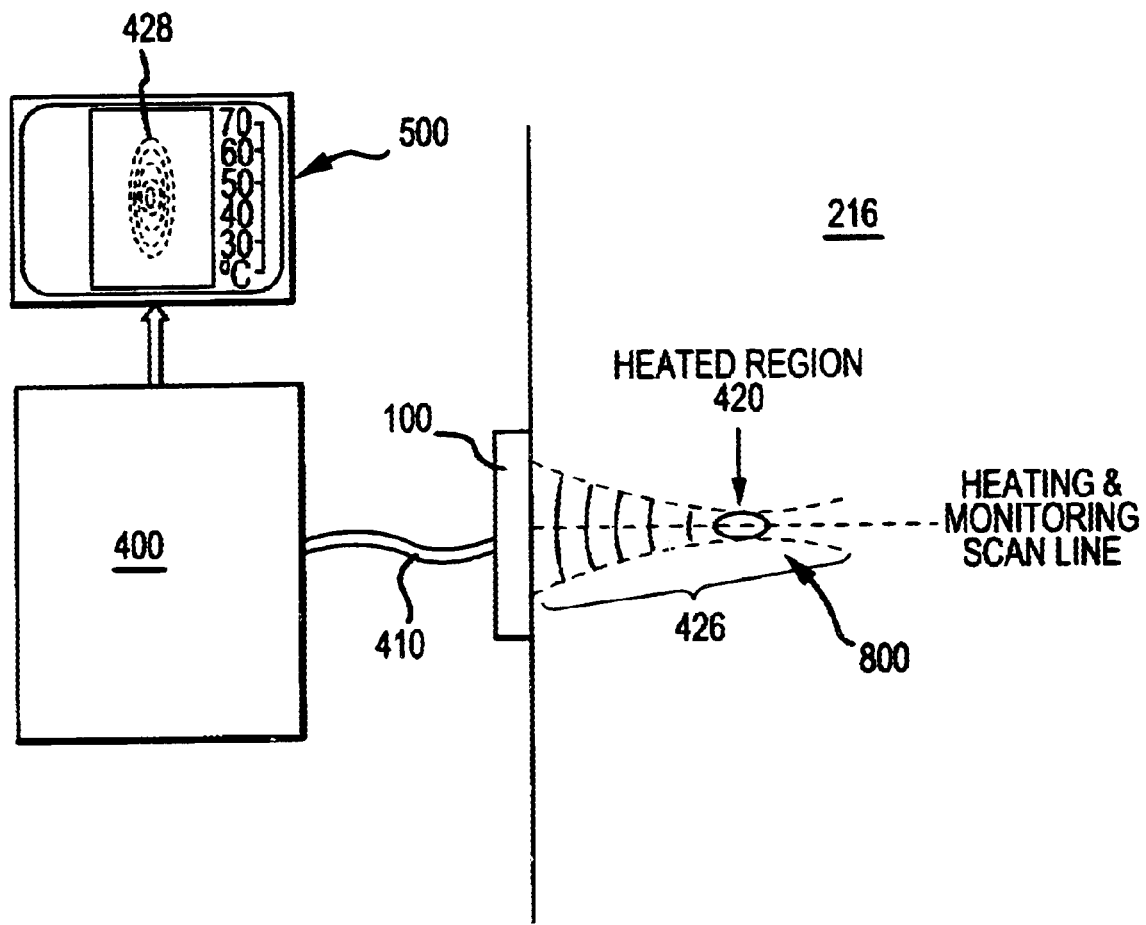
FIG. 4 is a diagram illustrating a temperature monitoring subsystem according to the present invention.

With reference to FIG. 4, a general schematic utilizing this approach is shown where transducer assembly 100 is used to heat a small region 800. As shown, the temperature monitoring subsystem 400 is connected to display 500. Temperature monitoring subsystem 400 is also connected to transducer assembly 100, such as by a suitable cable 410. In accordance with this aspect of the present invention, the whole volume is scanned, and by sweeping the pulse echo, the effective thermal dose (time/temperature history) (e.g. recrossed volume) can be determined. In the context of the present invention the term thermal dose relates to the temperature and time of duration integral function by which, for example, a determination of necrosity can be made.

With reference to FIG. 5, the echo waveform in a windowed region of a waveform A obtained before heating and a waveform B after heating can be examined, and based on the time-duration and spatial extent of the heated area, i.e. the time shift of the echo in the heated region and tissue and thermal properties, the temperature can be determined.

Alternatively, instead of evaluating the time shift, the echo amplitude in the windowed region could be examined. In accordance with this aspect of this embodiment of the present invention, when the amplitude of the signal in the windowed region begins to rapidly fall, the temperature will be in the 50° C. to 70° C. range. In this manner the effective necrosed volume can be determined.

It should be appreciated that in accordance with various aspects of the present invention, both echo time shifts and amplitude changes may be employed. For example, by scanning the windowed region in one, two, or three dimensions, a temperature map or image can be obtained.

Of course this technique may also be performed on an incremental basis to compensate for changes in temperature along some line, including, for example, before/after the hot spot. For example, by windowing out regions from the transducer to the region of interest and in each region computing the temperature from attenuation techniques or phase shifts, a temperature profile can be accurately determined.

With reference to FIG. 6, a temperature monitoring subsystem 400 which is interfaced to the acoustic transducer assembly 100 and monitor 500 is described below. The temperature monitoring subsystem 400 connected to the acoustic transducer assembly 100 via a cable 410 includes a control unit. The unit is operated so that the temperature mapping process as follows is properly conducted.

In particular, an acoustic pulse wave is first generated by a single transmitting element 110 among the linear array of the acoustic transducer assembly 100. The thus generated acoustic pulse wave propagates into the target tissue 800 and through any temperature gradients. Since the speed of sound in the target tissue 800 exhibits temperature dependency, the acoustic wavefronts will be sped up or slowed down in certain regions based on the temperature gradients existing in the target tissue 800. Upon reaching a boundary 850 used for reference, the acoustic wavefronts are reflected thereon so that the reflected wavefronts, i.e., the echoes come back towards the acoustic transducer assembly 100. Where they are detected by remaining elements 120 in the linear array. Upon the echoes returned from the target tissue 800 are detected by the acoustic transducer assembly 100, a certain signal is sent to the temperature monitoring subsystem 400 in which the time-of-flight data of the detected echoes (i.e., the returned acoustic wavefronts) which is a period of time required from the emission of a certain acoustic pulse to the detection of the corresponding echo (the reflected acoustic wave) is calculated. The above transmitting-and-detecting sequence is repeated for each unique transmitter-receiver combination to form a large data set.

Finally, using propagation path data, the obtained time-of-flight data is numerically converted into speed data of sound in the target tissue, and then further into a matrix of temperature values. Specifically, the speed V of sound (in this case, the speed of the ultrasonic wave) in the target tissue is expressed as follows:

$$V = V_0 + f(T) \tag{1}$$

where $V_0$ represents the speed of sound at a certain temperature in the target tissue, T is a temperature of the target tissue, and $f(T)$ is a function of T. Furthermore, the speed V of sound is also expressed as follows:

$$V = L/t \tag{2}$$

Analogous to the time-of-flight data, and use thereof as described herein, in accordance with various aspects of the present invention, the amplitude of the returned echoes can also be used to create an image of the acoustic attenuation.

As a result, from the above-mentioned expressions (1) and (2), the temperature T of the target tissue can be calculated based on the measured time-of-flight (the propagation time) data t with using values for L, $V_0$ and $f(T)$. Typical values for $V_0$ and $f(T)$ are known in the art or readily measured in experiments. On the other hand, the propagation path length L for the above calculation can be determined in several manners.

For example, a small biopsy needle, typically metallic, with a square cross-section can be placed in the target tissue until reaching a predetermined depth. Such a metallic needle provides a large amount of reflection of the acoustic waves, thereby functioning as an artificial reference boundary placed at a predetermined known depth in the target tissue.

Alternatively, instead of providing the artificial boundary, any natural boundaries existing in the target tissue can be used as the reference boundary which provides the basis of calculating the propagation path length. Such natural boundaries will include a tissue-to-air boundary, a tissue-to-water boundary, a tissue-to-bone boundary, and the like.

When any actual artificial or natural boundaries are not available in the target tissue as the reference boundary, an imaginary boundary or a virtual boundary can be produced. When one acoustic pulse or wave is emitted toward the target tissue at a time of zero (0) and the corresponding returning echo is detected at a time of X, then the specific pulse or wave has traveled in the target tissue over a distance which is approximately calculated as X times the speed of sound. Thus, the signal processing and analysis in the subsequent processes can be conducted based on this particular echo as the reference.

Analogous to the time-of-flight data, and use thereof as described herein, in accordance with various aspects of the present invention the amplitude of the returned echos can also be used to create an image of the acoustic attenuation.

The obtained temperature data is sent to the video display terminal 500 for visualization by the user, and also sent to the therapy subsystem 300 previously described for dynamic control of the heating process for the therapeutic treatment purposes.

In accordance with yet another embodiment of the present invention, temperature can be monitored using a tomographic approach (in addition to FIG. 6 embodiment). With reference to FIG. 7 the intersecting path of a transducer 100 having multiple elements is illustrated. The path of propagation is determined by the diffraction of the source and the properties of the medium. Along a path s the acoustic time-of-flight, τ will be the integral of the incremental delays over s $$\tau = \int \frac{ds}{v(s)} \tag{3}$$

It should be appreciated that the acoustic propagation will consist of phase retardation (additional delay) and diffraction loss (amplitude loss), refraction, and various tissues with associated speed of sound characteristics and each of these factors can, if desired, be included in the analysis.

In any event, by considering the intersecting paths, such as shown in FIG. 7, superimposed over a grid of pixels, where each pixel represents an area (volume) a tomographic configuration shown in FIG. 8 is obtained. By tracing the propagation and reception of the rays a solution to the velocity in each pixel from the matrix can be calculated according to the following equation:

$$[\tau] = [ds]\left[\frac{1}{v}\right] \tag{4}$$

where [τ] is a vector of measured delays, [ds] a matrix of known distances and [1/v] a vector of slowness, the reciprocal of the speed of sound (and thus temperature) in each pixel. Given the dependence of the speed of sound in tissue with temperature, the spatial temperature distribution in each pixel is thus determined. As noted briefly above, other factors including acoustic diffraction (beam spreading) and the temperature coefficients of tissue can be incorporated to enhance the accuracy of this method. In accordance with a particularly preferred aspect of the invention, the array can be rotated to allow for a three-dimensional mapping of temperature measurement.

By measuring the ray paths and then heating the region and rapidly re-measuring, an accurate spatial map of heating is obtainable, such map being substantially free of tissue motion artifacts.

As described above, the ultrasonic therapy system of the present invention includes an acoustic transducer assembly (in other words, the acoustic transducer subsystem), a therapy subsystem (in other words, a therapeutic heating subsystem), and a temperature monitoring subsystem as well as an appropriate display and control interface. This architecture non-invasively provides essential functions of real-time imaging and temperature monitoring of the treatment region during the therapeutic treatment process. This enables the user to obtain the feedback of the results of the therapeutic treatment process, resulting in improved control of the treatment process. By using the disclosed system of the present invention, safe, automated, and well-controlled procedures for the therapeutic treatment process are achievable at low cost and in only seconds or minutes of therapy. The use of the disclosed transducer capable of imaging, therapy, and monitoring allows precise geometric placement and monitoring of lesions, which has not previously been possible with prior art systems and/or methodologies.

With reference to FIGS. 9A–D and 10A–B, the performance of a transducer made in accordance with the present invention will now be described. Specifically, a 5×5 mm therapy transducer has been constructed in accordance with the present invention and the characteristics of that transducer determined.

Figure 9B:
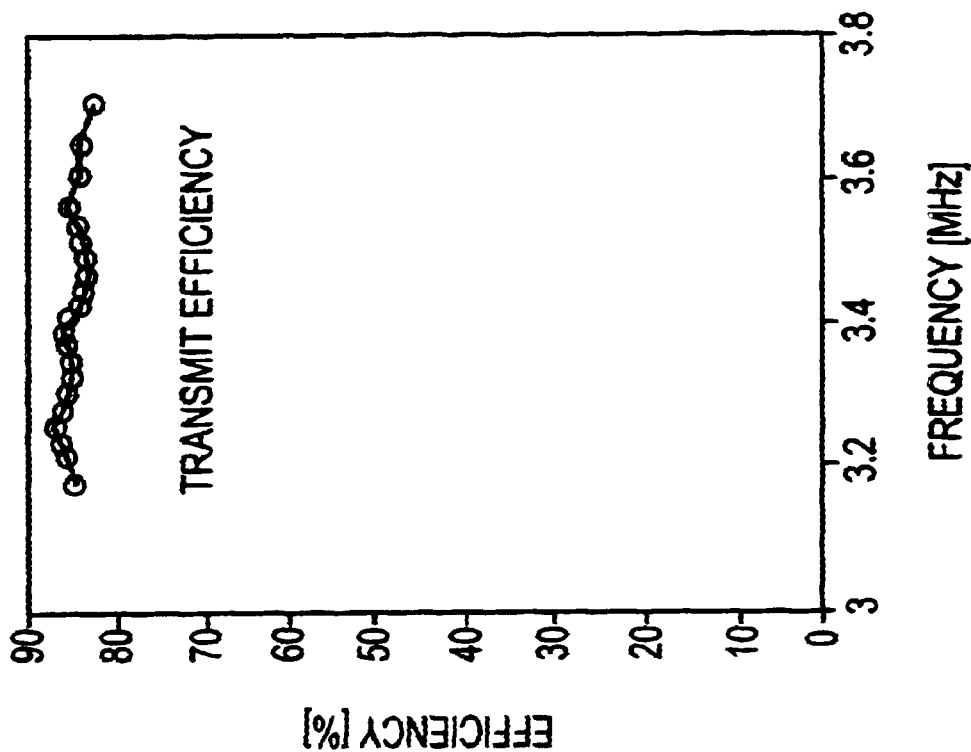
Figure 9A:
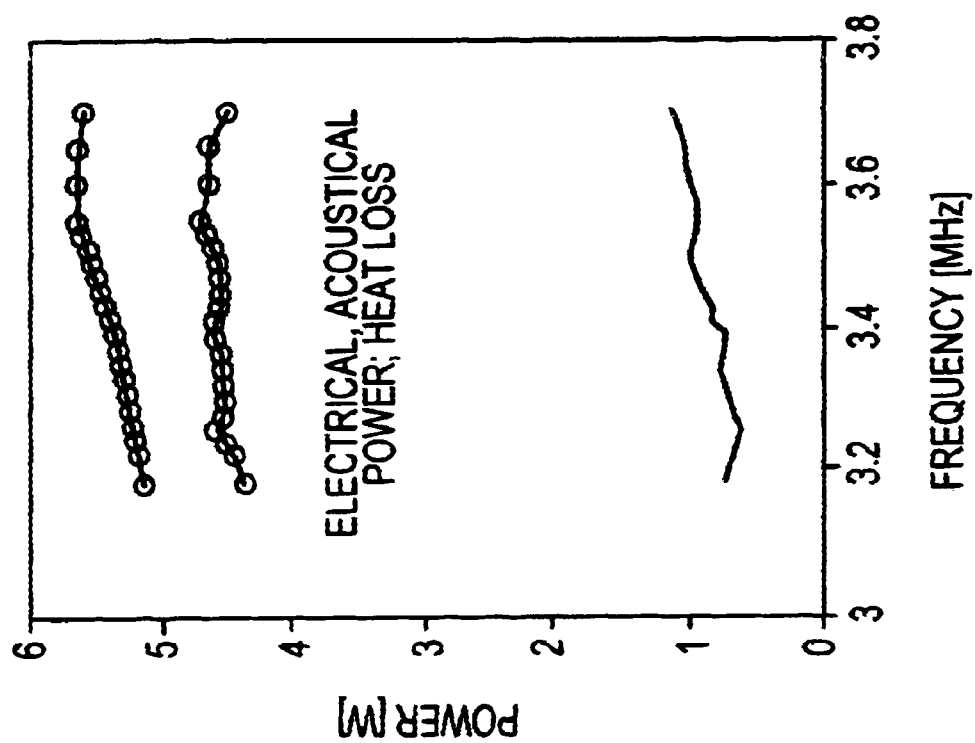

With respect to FIG. 9A, for example, the power versus frequency shown therein shows the electrical input, acoustical output and heat loss plots, respectively. As will be appreciated, each of these aspects are well within desirable ranges. Similarly, and with reference now to FIG. 9B, the transmit efficiency of the transducer over the range of 3–4 MHZ is on the order of above 80%, which, as will be appreciated by those skilled in the art, is more than acceptable. It should be appreciated that any suitable frequency range could be utilized.

Figure 9D:
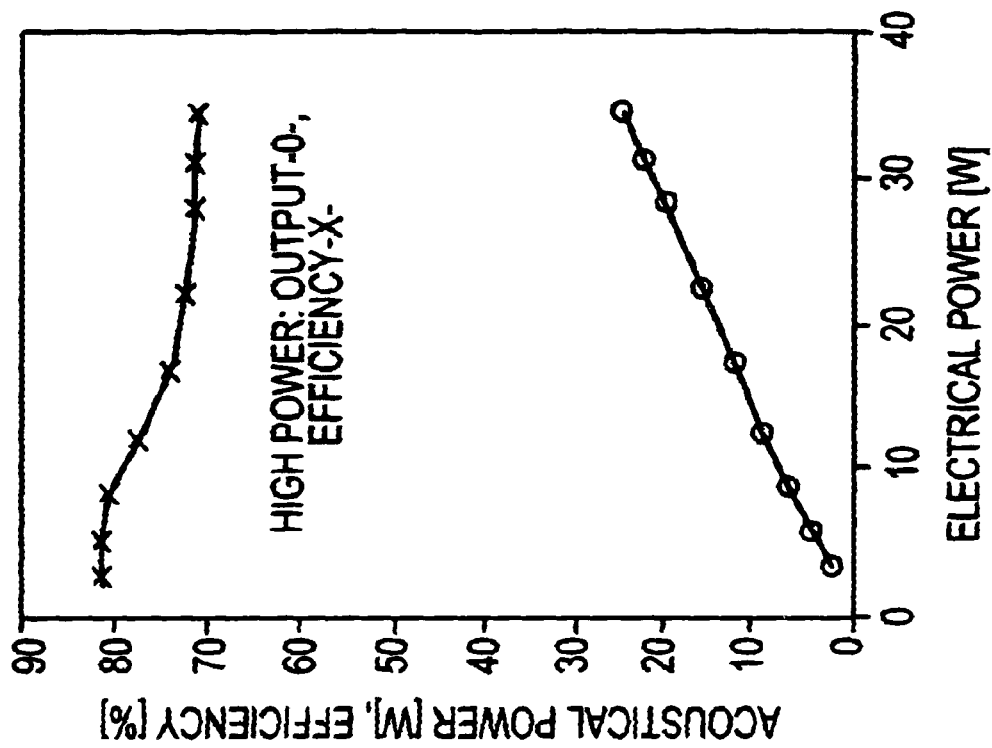
Figure 9C:
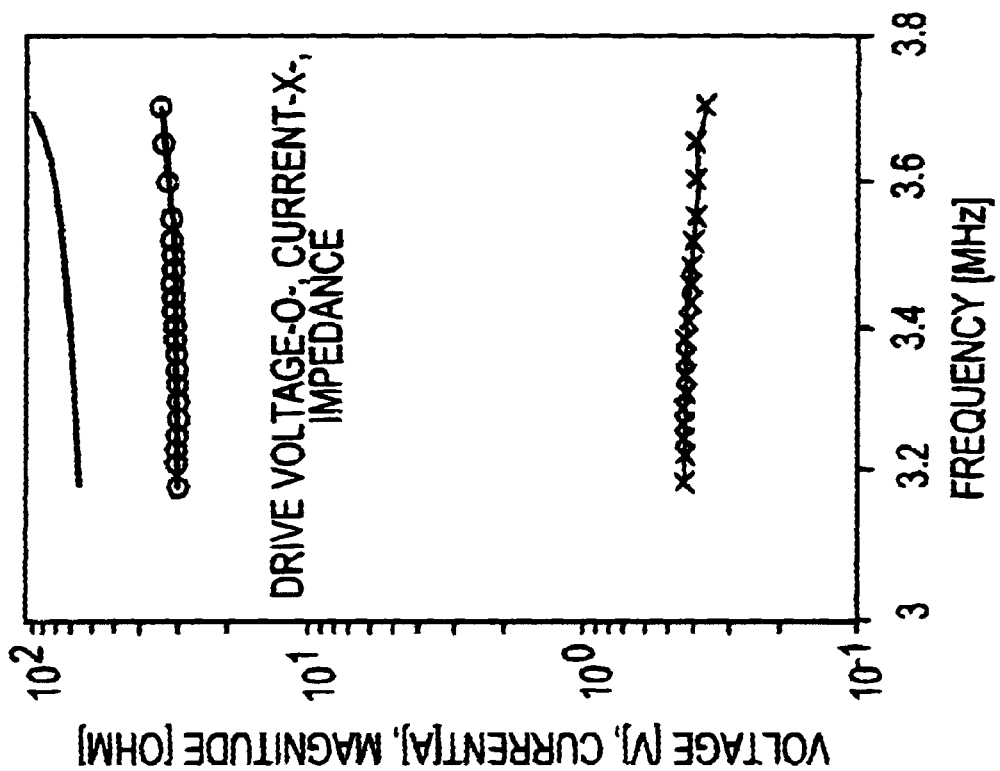

Referring now to FIG. 9C, the voltage, current and impedance magnitude of the transducer over a similar frequency range (e.g., 3–4 MHZ) is shown. In accordance with this particular embodiment, the drive voltage is on the order of about 30 volts, the current on the order of about 400 milliamps, and the impedance magnitude on the order of about 70 ohms.

Finally, with respect to FIG. 9D, the acoustical power at high power outputs is shown, and, as such, it can be seen that as electrical power is increased, the heating efficiency drops. However, over acceptable ranges, transducers made in accordance with the present invention exhibit acceptable performance.

Referring now to FIG. 10, the pulse echo waveform of the aforementioned exemplary transducer is shown in FIG. 10A and the frequency spectrum of the echo, without electrical tuning, is shown in FIG. 10B. As will be appreciated by those skilled in the art, the frequency spectrum and echo voltage plots evidence the usability and functioning of transducers made in accordance with the present invention. Specifically, it will be noted that the transducers exhibit high fractional bandwidth. Although the specific transducer used in gathering the data shown in FIG. 10 comprises a transducer with a single matching layer and no electrical tuning, providing two or more matching layers, as noted above, and electrically tuning the transducer, may enhance such characteristics to over 50% or more.

In accordance with another aspect of the present invention, a method and apparatus is provided for safely delivering an encapsulated medicant to a designated tissue region using ultrasound imaging and therapy. With reference again to FIG. 2, an exemplary apparatus of the present invention is generally illustrated. A single transducer 100, preferably a linear or curved linear array transducer, is connected to a control unit 200 by a cable 210. The control unit 200 drives the single transducer 100 to emit ultrasonic wave energy through the body of a patient 216. A video display terminal 500 is connected to the control unit 200 in order to view the imaging.

Thermosensitive or heat-activated, liposome encapsulated medicants (not shown) are administered to a region of interest 800 under the skin layer 220 of the patient 230. The liposome encapsulated medicants are preferably suspended in an aqueous material such as water or saline. Once suspended, the liposome encapsulated medicants can be administered to the desired tissue region of interest in a number of ways including intravascularly, intra lymphatically, parenterally, subcutaneously, intramuscularly, ultra peritoneally, interstitially, hyperbarically, orally, or intratumorly. The lipids used in constructing the thermosensitive liposome may be either natural or synthetic and may include any of those lipids described in U.S. Pat. 5,348,016, which is herein incorporated by reference in its entirety, provided that the melt temperature of any resulting liposome is not greater than 44 degrees C. Liposome preparation may also be carried out using the materials and/or processes described in U.S. Pat. No. 5,257,970, issued to Dougherty, for creating heat-sensitive liposomes, which is also herein incorporated by reference in its entirety. Preferably, the liposomes should be constructed such that they have a melt temperature of about 40 to 44 degrees C., at least greater than body temperature. Further, the thermosensitive liposomes are preferably designed such that they are only able to dissolve and release within about ½ of a degree of a defined temperature, for example, plus or minus 0.1 degrees C. to plus or minus 0.9 degrees C. Liposomes having this temperature sensitive threshold will enhance the capability of safely delivering the medicant to the tissue by avoiding fibrosis, the melting of fat, and cavitation.

The transducer 100 is placed adjacent to the skin 220 of the patient 216. The control unit 200 drives the transducer 100 to emit ultrasound frequencies which are appropriate for imaging, preferably in the range of about 2 to 20 MHz.

Once the region of interest 800 is located by using ultrasound imaging, a control unit, such as control unit 300, may then be used to drive the transducer 100 to emit therapeutic ultrasound energy 324 to the region of interest 800 to induce a therapeutic effect as shown in FIG. 3. More particularly, ultrasound energy is emitted which is capable of heating the region of interest 800 which includes heating of the liposomes encasing the medicant. The region of interest 800 is preferably heated to a temperature of about 40–43 degrees C. This temperature is sufficient to melt the liposomes thereby releasing the medicant into the surrounding tissue.

With reference again to FIG. 4, a schematic drawing of the apparatus of the present invention is shown wherein the temperature of the region of interest 800 is being monitored in order to determine if the desired temperature threshold has been reached. The control unit 400 drives the transducer 100 to emit ultrasonic wave energy into the patient 216 to monitor the temperature of the region of interest 800. The transducer 100 then detects sound waves 426 reflected from the region of interest 800 and translates the data into thermal images 428.

As discussed above, various methods may be utilized for monitoring the temperature. One method for monitoring the temperature employs the calculation of the temperature according to changes in the time-of-flight and amplitude of the ultrasound waves relative to the unheated tissue state. As discussed, FIG. 5 shows an ultrasonic waveform A immediately before the therapeutic heating of a tissue region and another ultrasonic waveform B after therapeutic heating of the same tissue region. In the windowed time segment 502 where therapeutic heating occurs, ultrasonic echoes will be shifted in time and amplitude relative to the unheated state due to the temperature dependence (increase) of the speed of sound and acoustic attenuation in the tissue. A time-shift and amplitude reduction of waves in the heated tissue region yields the temperature based on the known functions of speed of sound and acoustic attenuation versus temperature in tissue. Thusly, a 1-, 2-, or 3-dimensional temperature profile can then be obtained by firing several acoustic scan lines through the tissue via mechanical and/or electronic means.

FIG. 11A and FIG. 11B show another method for acoustically monitoring the temperature of the region of tissue treated with the apparatus of the present invention. A natural or artificial boundary is used to reflect a myriad of ultrasound waves back to the transducer after crossing the treatment region whereby the time-of-flight and amplitude of the received echoes are employed to create a map of the speed of sound and acoustic attenuation by means of tomographic principles. The tissue temperature is derived based on the known functions of speed of sound and acoustic attenuation versus temperature and tissue. For example, a transducer 100 composed of N elements 15 may be pulsed on any one element and echoes can be received on all of the remaining elements after reflecting off of the boundary 1102. By repeating this sequence, a total of N (N−1)/2 unique transmit-receive combinations are formed in addition to another N single-element pulse-echo combinations. This yields a total of M=N(N+1)/2 unique projections. Accordingly, this large number of known flight times and amplitudes integrated over known paths of propagation may be used to determine the speed of sound and acoustic attenuation of the path of propagation. The propagation region can be divided into several areas or volumes 1104. Since the temperature coefficient of the speed of sound is known, changes in the speed of sound can be directly related to changes in temperature, thereby allowing the temperature in an area or volume of tissue to be mapped.

Moreover, varying types of array transducers may be used to direct the ultrasound energy. For example, if a linear array transducer is used to transmit the ultrasound energy, we can assume that each array element is a point source that radiates a spherically shaped wavefront into the medium. The array element farthest from the focus point is excited first. The remaining elements are excited at the appropriate time intervals so that the acoustic signals from all the elements reach the focal point at the same time. The net acoustical signal is the sum of the signals that have arrived from each source. The contributions from every element add in phase to produce a peak in the acoustic signal at the focal point. Outside of the focal point, some of the contributions add out of phase thereby reducing the signal relative to the peak.

After measurement of the temperature, the treatment is stopped if the threshold temperature has been reached and the treatment continues if the threshold temperature has not been reached by programming the control unit 300 to drive the transducer 100 to emit additional therapeutic ultrasound frequencies to the region of interest 800. The temperature of the region of interest is again monitored. If the threshold temperature is achieved the treatment is stopped. If the threshold temperature is not achieved, this same sequence is repeated until the threshold temperature is achieved at which time the treatment will stop. The control unit 300 also includes a programmable feature for automatically disabling the therapeutic ultrasound treatment when the region of interest 800 reaches a certain designated temperature. In this case, the preferred designated temperature for disabling the therapeutic ultrasound is about 44 degrees C. since severe damage to the tissue can occur above that temperature.

FIG. 12 is a flowchart showing an exemplary method of the present invention for safely delivering an encapsulated medicant to a region of interest within the body using ultrasound. Step 1202 includes the administration or disposition of thermosensitive liposomes containing medicants within the body. As previously described above, the liposomes can be delivered to a region of interest within the body in a number of ways including, but not limited to, intravascularly, intra lymphatically, parenterally, subcutaneously, intramuscularly, intra peritoneally, interstitially, hyperbarically, orally, or intratumorly. The region of interest containing the thermosensitive liposomes is located in step 1204 using ultrasound imaging. In step 1206, therapeutic ultrasound is used to heat the region of interest. The temperature of the region of interest is monitored in step 1208 by employing a method which calculates the temperature according to the difference in flight time and amplitude of the ultrasonic waves. In step 1210, a determination is made as to whether the threshold temperature has been reached, with the threshold temperature being sufficient to melt the walls of the liposomes in order to release the medicant contained therein. If the threshold temperature has been reached 1214, a determination is made as to whether there are any more regions of interest for treatment in step 1218. If there are no more regions of interest for treatment 1220, then the treatment is finished in step 1222. If there are more regions of interest for treatment 1216, then a return is made to step 1204 in which ultrasound imaging is used to locate another region of interest.

Turning back to step 1216, if the temperature threshold is not reached 1212, then a return is made to step 1206 where therapeutic ultrasound is again applied to heat the region of interest. The temperature of the region of interest is again monitored in step 1208 to determine if the threshold temperature has been reached in step 1210. This loop of processes is then repeated until the threshold temperature has been reached 1214.

Although a sequence of steps is described in accordance with an exemplary method of the present invention for safely delivering an encapsulated medicant to a region of interest within the body using ultrasound, it should be noted that the sequence of various steps may be alternated in various manners. For example, the temperature of the region of interest 800 can be monitored in step 1208 prior to the step 1206 for heating the region of interest. Various other sequences are also comtemplated by the present invention.

Numerous applications exist for the method and apparatus of the present invention. One extremely important application involves using liposorne directed drug delivery and hyperthermic treatment in chemotherapy. The use of ultrasound for the targeted heating of malignant tissue to increase the temperature of the tissue, and to further stimulate the temperature-dependent drug release from liposomes containing chemotherapeutic agents, can greatly improve the selective localization of chemotherapy drugs while reducing the cytotoxic activity that can occur with chemotherapy drugs when using hyperthermic treatment alone.

In an effort to establish the possible success of using ultrasound to target drugs encapsulated in long-circulating, thermosensitive liposomes and to potentiate the activity of the drugs in the condition of hyperthermia, in vivo studies were performed with mice.

Liposomes were prepared with Dipalnitoyl-dl-phosphatidylcholine/ Distearoyl-dI-phosphatidyicholine (DPPC/DSPC) in a 9:1 molar ratio and an appropriate amount of ganglioside Gml by a freezing/thawing procedure followed by filtration through Nucleopore filters (0.2 micron). 6-Carboxyfluorescein (6.CF) was used as a tracer agent and the thermal stability of the liposomes was determined by measuring the leakage of 6-CF from the liposomes at 37 degrees C. and 42 degrees C. in Phosphate Buffered Saline (PBS) or calf serum.

Mice were then injected intravenously with free 6-CF or encapsulated 6-CF. Local hyperthermia was performed using an ultrasonicator. The ultrasonicator was used to produce a 42 degrees C. temperature five minutes after liposome administration and was continued for ten minutes. After completion of the hyperthermia treatment, blood was collected and major organs were excised and stored at −20 degrees C. until they were assayed. Fifty to one hundred milligrams of tissue were used for the measurement of 6-CF concentration. Samples were homogenized, centrifuged at 20,000 revolutions per minute for thirty minutes, and the resulting supenatant was used for fluorometry.

Results were as follows:

| | Tissue Distribution of Fluorescent Probe Following Intravenous Administration of Thermolabile Liposomes and Ultrasonication of Targeted organs | | |
|---|---|---|---|
| | | % of Total Injected Fluorescence | |
| N | Organ/Tissue | Control | Sonication |
| 1 | Liver | 25 ± 3 | 44 ± 5 |
| 2 | Spleen | 18 ± 3 | 28 ± 4 |
| 3 | Lung | 13 ± 2 | 23 ± 4 |

The present invention directed toward a method and apparatus for controlling and safely delivering mendicants to a tissue region using ultrasound exhibits many advantages over the prior art including non-invasive heating, high spatial resolution with localized therapy, a lower threshold temperature, reduced acoustic power requirement, and simplified equipment. Moreover, although use of a single transducer configured for imaging, temperature monitoring and heating is contemplated, multiple transducers may also be utilized for controlling and safely delivering medicants to the tissue region.

It will be appreciated that the invention described herein offers various advantages over the prior art techniques. However, the various embodiments were chosen and described in order to explain the principles of the invention and its practical application to enable others of ordinary skill in the art to best utilize the invention in various embodiments and with various modifications as are suited to the particular use contemplated. It is intended that the scope of the invention be defined by the claims attached hereto.

We claim:

1. A method for the controlled delivery of a medicant to a region of interest within a patient's body comprising the steps of:

administering a thermosensitive liposome encased medicant to the region of interest;

locating the region of interest containing the thermosensitive liposome using ultrasound imaging with a single ultrasound transducer;

applying ultrasound therapy with the single ultrasound transducer to heat the region of interest containing the thermosensitive liposome;

monitoring the temperature of the region of interest containing the thermosensitive liposome using ultrasound imaging with the single ultrasound transducer to create a temperature profile; and alternating application of ultrasound therapy and ultrasound imaging with the single ultrasound transducer until a predetermined temperature threshold is reached.

2. The system of claim 1 wherein said step of monitoring the temperature of the region of interest comprises the step of automatically discontinuing the heating of the tissue region when the temperature of the tissue region rises above a melt temperature for said thermosensitive liposome.

3. The method of claim 1 wherein said step of administering a thermosensitive liposome encased medicant comprises the step of introducing a thermosensitive liposome having a melt temperature variance of about 0.5 degrees C.

4. The method of claim 1 wherein said step of administering a thermosensitive liposome encased medicant comprises the step of introducing at least one of a therapeutic drug, a reagent, and a bioactive compound.

5. An apparatus for safely delivering a medicant contained within a thermosensitive liposome to a region of tissue contained within a patient's body comprising:

means for introducing a thermosensitive liposome containing a medicant to a predetermined body tissue region;

a single ultrasound transducer for imaging the tissue region, monitoring a temperature profile of the tissue region and heating the thermosensitive liposome disposed in the tissue region; and a control unit for continuously driving the ultrasound transducer to determine the temperature profile of the tissue region.

6. The apparatus of claim 5 further comprising a visual display terminal for imaging the temperature profile.

7. The apparatus of claim 5 wherein the ultrasound transducer includes means to heat the tissue region to a temperature of at least 43 degrees C. and greater than a melt temperature of the liposome.

8. The apparatus of claim 5 wherein the ultrasound transducer includes means to heat the tissue region with high spatial resolution.

* * * * *